United States Patent
Arimitsu

(10) Patent No.: US 12,399,427 B2
(45) Date of Patent: Aug. 26, 2025

(54) PHOTOBASE GENERATOR, COMPOUND, PHOTOREACTIVE COMPOSITION AND REACTION PRODUCT

(71) Applicant: Tokyo University of Science Foundation, Tokyo (JP)

(72) Inventor: Koji Arimitsu, Tokyo (JP)

(73) Assignee: Tokyo University of Science Foundation, Tokyo (JP)

( * ) Notice: Subject to any disclaimer, the term of this patent is extended or adjusted under 35 U.S.C. 154(b) by 543 days.

(21) Appl. No.: 17/788,770

(22) PCT Filed: Dec. 24, 2020

(86) PCT No.: PCT/JP2020/048583
§ 371 (c)(1),
(2) Date: Jun. 24, 2022

(87) PCT Pub. No.: WO2021/132520
PCT Pub. Date: Jul. 1, 2021

(65) Prior Publication Data
US 2023/0089021 A1 Mar. 23, 2023

(30) Foreign Application Priority Data
Dec. 26, 2019 (JP) ................. 2019-237416

(51) Int. Cl.
*G03F 7/004* (2006.01)
*C07D 213/75* (2006.01)
*C08K 5/3432* (2006.01)

(52) U.S. Cl.
CPC ......... *G03F 7/0045* (2013.01); *C07D 213/75* (2013.01); *C08K 5/3432* (2013.01)

(58) Field of Classification Search
None
See application file for complete search history.

(56) References Cited

U.S. PATENT DOCUMENTS

| | | | |
|---|---|---|---|
| 2011/0086311 A1 | 4/2011 | Katayama et al. | |
| 2022/0298268 A1* | 9/2022 | Arimitsu | C09K 3/00 |
| 2022/0340528 A1* | 10/2022 | Arimitsu | C07D 295/192 |

FOREIGN PATENT DOCUMENTS

CN 106187891 A 12/2016

OTHER PUBLICATIONS

Li, H.-M., Yu, S.-P., Fan, T.-Y., Zhong, Y., Gu, T., Wu, W.-Y., Zhao, C., Chen, Z., Chen, M., Li, N.-G., Wang, X.-L .—Design, synthesis, and biological activity evaluation of BACE1 inhibitors with antioxidant activity, Drug Dev. Res,2020, 81, 106-214 (Year: 2020).*
Arimitsu et al. "Application to Photoreactive Materials of Photochemical Generation of Superbases with High Efficiency Based on Photodecarboxylation Reactions" Chem.Mater.2013, 25, 4461-4463.
Cameron et al. "Photogeneration of Organic Bases from o-Nitrobenzyl-Derived Carbamates" J.Am.Chem.Soc.1991, 113, 4303.
Singh et al., "Biological Studies of some New Substituted Phenyl pyrazol pyridin-2-amine derivatives", International Journal of ChemTech Research, 2011, vol. 3, No. 2, 892-900 p. 895 Table-I Compound No. 2c.
Singh et al., "Synthesis and biological evaluation of some pyrazolinylpyridines and pyrazolylpyridines", Archiv der Pharmazie, 2006, 339 (1), 24-31 pp. 26, 28, Table 1, 2, Compound 2c.
Arimitsu Koji et al: "Photobase generators derived from trans-o-coumaric acid for anionic UV curing systems without gas generation", Journal of Polymer Science Part A: Polymer Chemistry, vol. 53, No. 10, Mar. 3, 2015 (Mar. 3, 2015), pp. 1174-1177, XP093004170, US ISSN: 0887-624X, DOI: 10.1002/pola.27552 Retrieved from the Internet: URL:https://api.wiley.com/onlinelibrary/tdm/v1/articles/10.1002%2Fpola. 27552> *Scheme2*.

* cited by examiner

Primary Examiner — Anca Eoff
(74) Attorney, Agent, or Firm — Banner & Witcoff, Ltd.

(57) ABSTRACT

A photobase generator, includes a compound including a first skeleton represented by the following formula (a); and a second skeleton including a nitrogen atom bonding to a bonding position of the first skeleton to form an amide group, and a pyridine skeleton in addition to the nitrogen atom, in which the compound generates a base in which a hydrogen atom is bonded with the nitrogen atom of the second skeleton by light irradiation. In formula (a), G is a divalent aromatic group, and * represents the bonding position with the nitrogen atom.

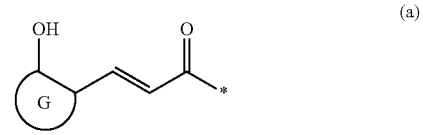

(a)

5 Claims, 13 Drawing Sheets

PHOTOBASE GENERATOR, COMPOUND, PHOTOREACTIVE COMPOSITION AND REACTION PRODUCT

RELATED APPLICATIONS

This application is a National Stage Application under 35 U.S.C. 371 of co-pending PCT application PCT/JP2020/048583 designating the United States and filed Dec. 24, 2020; which claims the benefit of JP application number 2019-237416 and filed Dec. 26, 2019, each of which are hereby incorporated by reference in their entireties.

TECHNICAL FIELD

The present invention relates to a photobase generator, a compound, a photoreactive composition and a reaction product.

TECHNICAL BACKGROUND

Photopolymerizable materials to be polymerized when irradiated with light are widely practically used, and hold predominant positions in the fields of, for example, electronic materials or printing materials, because polymerization reactions thereof can be precisely controlled by relatively simple operations.

Photopolymerizable materials which have been heretofore actively studied are, for example, a radical polymerization resin composition including a photoinitiator that generates radical species by exposure, and a radical-polymerizable monomer or oligomer, and an acid catalyst-based resin composition including a photoacid generator that generates acid by exposure, and a monomer or oligomer to be polymerized by the action of an acid.

Base catalyst-based photopolymerizable materials are also known as photopolymerizable materials, such a base catalyst-based photopolymerizable material including a photobase generator that generates base by exposure, and a monomer or oligomer to be polymerized by the action of a base. A photobase generator known is, for example, an ionic photobase generator corresponding to a salt of a strong base such as guanidine and a carboxylic acid (see, for example, Non-Patent Literature 1). Such an ionic photobase generator allows a decarboxylation reaction to progress in a carboxy group by exposure, and generates a base by release of a strong base forming a salt together with the carboxy group.

However, such an ionic photobase generator has the problem of being low in stability during storage and low in solubility, although high in reactivity. A resin composition using such an ionic photobase generator also has the problem of being low in stability.

On the contrary, non-ionic photobase generators have also been studied. A non-ionic photobase generator known is, for example, a non-ionic photobase generator that is a carbamate having a nitrobenzyl skeleton, in which a base is generated by progression of a decarboxylation reaction and release of a primary amine or a secondary amine by exposure (see, for example, Non-Patent Literature 2). Such a non-ionic photobase generator allows the above problems about ionic photobase generators to be solved.

[Non-Patent Literature 1] K. Arimitsu, R. Endo, Chem. Mater. 2013, 25, 4461-4463.

[Non-Patent Literature 2] J. F. Cameron, J. M. J. Frechet, J. Am. Chem. Soc. 1991, 113, 4303.

SUMMARY OF INVENTION

Technical Problem

The non-ionic photobase generator as disclosed in Non-Patent Literature 2 has a problem that a decarboxylation reaction occurs with the generation of a base by exposure.

Further, when irradiated with light and heated, a photobase generator capable of preparing a photoreactive composition having excellent reactivity of a base-reactive compound (for example, an epoxy compound) is required.

An object of the present disclosure is to provide a photobase generator and a compound capable of preparing a photoreactive composition that has excellent reactivity of a base-reactive compound when irradiated with light and heated and that does not cause a decarboxylation reaction when irradiated with light, a photoreactive composition that has excellent reactivity of a base-reactive compound when irradiated with light and heated and that does not cause a decarboxylation reaction when irradiated with light, and a reaction product obtained by reacting the photoreactive composition.

Solution to Problem

Examples of means for solving the above problem are shown below.

<1> A photobase generator, comprising a compound including: a first skeleton represented by the following formula (a); and a second skeleton including a nitrogen atom bonding to a bonding position of the first skeleton to form an amide group, and a pyridine skeleton in addition to the nitrogen atom, wherein the compound generates a base in which a hydrogen atom is bonded with the nitrogen atom of the second skeleton by light irradiation.

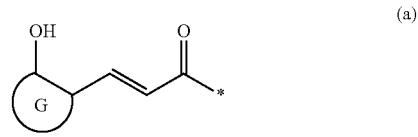

(a)

In formula (a), G is a divalent aromatic group, and * represents the bonding position with the nitrogen atom.

<2> The photobase generator according to <1>, wherein the second skeleton includes an aminopyridine skeleton.

<3> A compound comprising: a first skeleton represented by the following formula (a); and a second skeleton including a nitrogen atom bonding to a bonding position of the first skeleton to form an amide group, and a pyridine skeleton in addition to the nitrogen atom, wherein the compound generates a base in which a hydrogen atom is bonded with the nitrogen atom of the second skeleton by light irradiation.

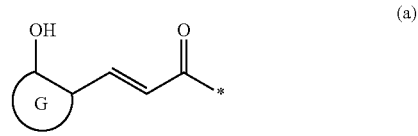

(a)

In formula (a), G is a divalent aromatic group, and * represents the bonding position with the nitrogen atom.

<4> The compound according to <3>, wherein the second skeleton includes an aminopyridine skeleton.

<5> A photoreactive composition, comprising: the photobase generator according to <1> or <2>; and a base-reactive compound, wherein the base-reactive compound is a compound having a functional group that is converted, by action of a base, into a group exhibiting reactivity, or a compound having a group that reacts in response to action of a base.

<6> A reaction product obtained by reacting the photoreactive composition according to <5>.

Advantageous Effects of Invention

The invention can provide a photobase generator and a compound capable of preparing a photoreactive composition that has excellent reactivity of a base-reactive compound when irradiated with light and heated and that does not cause a decarboxylation reaction when irradiated with light, a photoreactive composition that has excellent reactivity of a base-reactive compound when irradiated with light and heated and that does not cause a decarboxylation reaction when irradiated with light, and a reaction product obtained by reacting the photoreactive composition.

DESCRIPTION OF EMBODIMENTS

Figure 1:
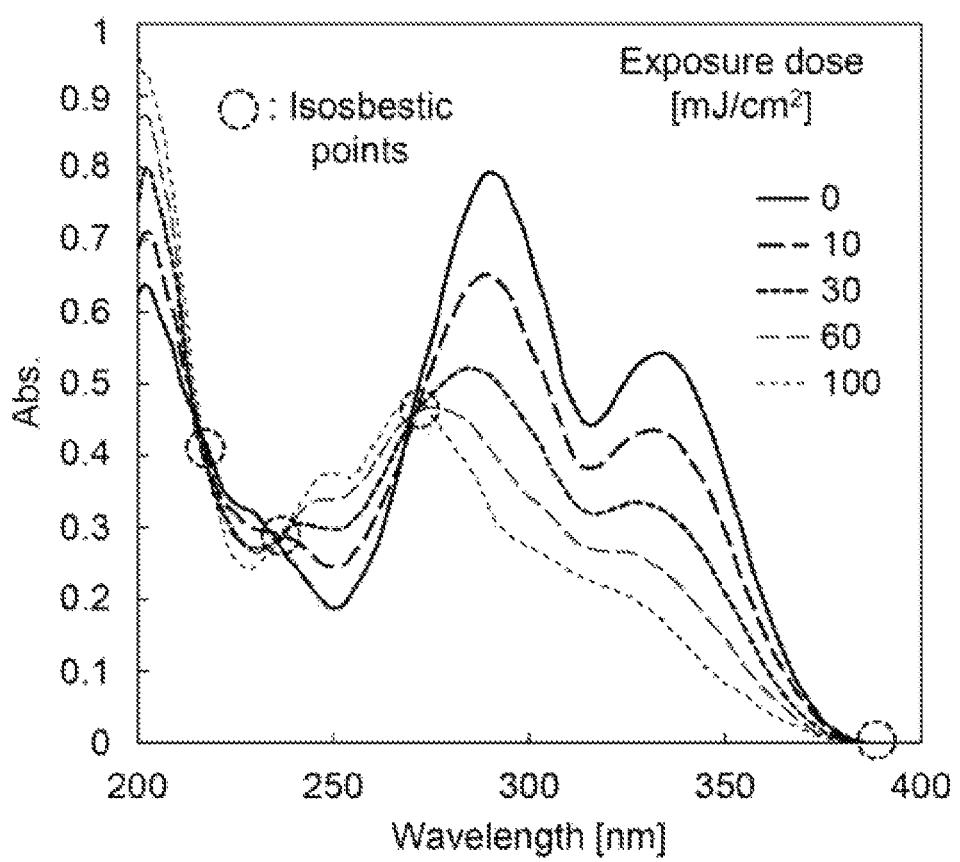
FIG. 1 is data that illustrates the measurement results of the absorbance of a compound (1)-1 in Test Example 1.

In the present disclosure, a numerical range specified by way of using the expression "(from) . . . to . . . " includes the numerical values before and after the word "to" as the lower limit value and the upper limit value.

In the numerical ranges described in a stepwise manner in the present disclosure, the upper limit value or the lower limit value described in one numerical range may be replaced with the upper limit value or the lower limit value of another numerical range described in a stepwise manner. In the numerical ranges described in the present disclosure, the upper limit value or the lower limit value of the numerical ranges may be replaced with the values shown in the Examples.

In the present disclosure, each component may include plural substances corresponding to the component. When plural substances corresponding to each component are present in a composition, the amount of each component means the total amount of the plural substances present in the composition unless otherwise specified.

[Photobase Generator]

A photo base generator in the present disclosure includes a compound including: a first skeleton represented by the following formula (a); and a second skeleton including a nitrogen atom bonding to a bonding position of the first skeleton to form an amide group, and a pyridine skeleton in addition to the nitrogen atom, wherein the compound generates a base in which a hydrogen atom is bonded with the nitrogen atom of the second skeleton by light irradiation.

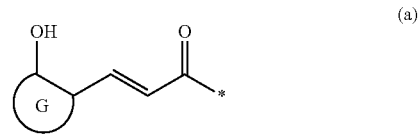

(a)

In formula (a), G is a divalent aromatic group, and * represents the bonding position with the nitrogen atom.

For example, the photobase generator of the present disclosure is used for preparation of a photoreactive composition capable of manufacturing a reaction product by reacting a base-reactive compound by light irradiation and heating. More specifically, by irradiating the photoreactive composition including the base generator and the base photoreactive composition with light, a base is generated from the base generator, and a functional group included in the base-reactive compound in the photoreactive composition is converted, by action of a base, into a group exhibiting reactivity, or a functional group included in the base-reactive compound reacts in response to action of a base. Thus, the aforementioned photoreactive composition is irradiated with light to generate the base, thereby allowing the base-reactive compound included in the photoreactive composition to be reacted, and the reaction product is obtained.

The photobase generator of the present disclosure includes a compound (in the present disclosure, also referred to as "compound (1)") including the first skeleton represented by the formula (a); and the second skeleton including a nitrogen atom bonding to the bonding position of the first skeleton to form an amide group, and a pyridine skeleton in addition to the nitrogen atom, in which the compound (1) generates a base in which a hydrogen atom is bonded with the nitrogen atom of the second skeleton by light irradiation. In the compound (1), as shown by the following formula (i), it becomes a cis isomer by light irradiation, and then the oxygen atom of the hydroxyl group in the general formula (a) was bonded to the carbonyl carbon in the general formula (a), and the nitrogen atom in the second skeleton, which was bonded to the carbonyl carbon, dissociates and is bonded to a hydrogen atom. As a result, a compound represented by the following general formula (1') and an amine compound represented by HX are generated. The generated amine compound is a base in which a hydrogen atom is bonded to the nitrogen atom in the second skeleton.

The compound (1) is a non-ionic photobase generator, and unlike conventional ionic photobase generators, it has high stability during storage and high solubility, and the photoreactive composition using the compound (1) has high stability. Further, because the photoreactive composition using the photobase generator including the compound (1) generates a base in which a hydrogen atom is bonded to the nitrogen atom of the second skeleton having the pyridine skeleton, for example, when the base-reactive compound is an epoxy compound, the reactivity of the base-reactive compound when irradiated with light and heated is excellent.

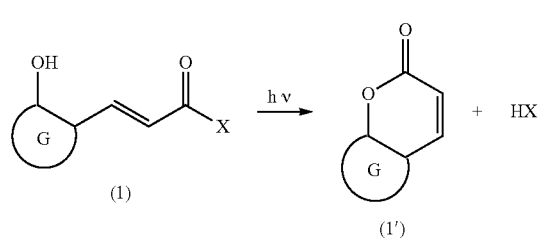

(i)

(1) → (1') + HX

As a conventionally known non-ionic photobase generator, for example, a carbamate having a nitrobenzyl skeleton shown below is known. When a carbamate having such a nitrobenzyl skeleton is irradiated with light, a decarboxylation reaction proceeds as shown in the following formula (ii), and a base (in the following reaction formula, a primary amine) is generated.

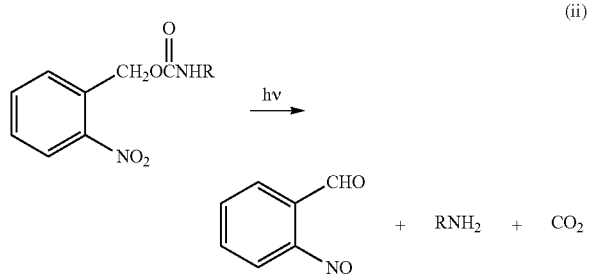

(ii)

On the other hand, in the compound (1) included in the photobase generator of the present disclosure, as shown in the aforementioned formula (1), a decarboxylation reaction does not occur by light irradiation. As a result, the generation of bubbles due to the generation of carbon dioxide, and the decrease in strength or the like when the reaction product is a cured product, can be reduced.

In the formula (a), G is a divalent aromatic group, and a hydroxyl group and —CH=CH—C(=O)—* are bonding with G.

The respective bonding positions of the hydroxyl group and —CH=CH—C(=O)—* to G are in an ortho-position. In other words, the atom to which the hydroxyl group is bonding and the atom to which —CH=CH—C(=O)—* is bonding, among atoms included in the ring skeleton of G, are adjacent to each other in the ring skeleton of G and are directly bonding to the ring skeleton.

The aromatic group in G may be any of a divalent aromatic hydrocarbon group or a divalent aromatic heterocyclic group, or may be a divalent group (in the present disclosure, such a group is regarded as an aromatic heterocyclic group) obtained by ring fusion of an aromatic hydrocarbon group and an aromatic heterocyclic group.

The aromatic hydrocarbon group and the aromatic heterocyclic group may have a substituent.

The "aromatic hydrocarbon group having a substituent" means that one or more hydrogen atoms included in the aromatic hydrocarbon group is substituted with any group (substituent) other than a hydrogen atom.

The "aromatic heterocyclic group having a substituent" means that one or more hydrogen atoms included in the aromatic heterocyclic group is substituted with any group (substituent) other than a hydrogen atom.

The aromatic group in G may be either monocyclic or polycyclic, and the number of atoms (number of ring members) included in the ring skeleton is not particularly limited, and is preferably from 3 to 20.

Examples of the aromatic hydrocarbon group as the aromatic group in G include a 1,2-phenylene group, a naphthalene-1,2-diyl group, a naphthalene-2,3-diyl group, a toluene-2,3-diyl group, a toluene-3,4-diyl group, an o-xylene-3,4-diyl group, an o-xylene-4,5-diyl group, an m-xylene-4,5-diyl group, a p-xylene-2,3-diyl group, an anthracene-1,2-diyl group, and an anthracene-2,3-diyl group. One or more hydrogen atoms in the aromatic hydrocarbon group may be each substituted with a substituent, for example, the aromatic hydrocarbon group or alkyl group exemplified. The aromatic hydrocarbon group having such a substituent preferably has 6 to 20 carbon atoms also including carbon atom(s) of the substituent.

The alkyl group (hereinafter, sometimes referred to as "substituent alkyl group") with which one or more hydrogen atoms of the aromatic hydrocarbon group exemplified are/is substituted may be any of a linear, branched, or cyclic alkyl group, and may be any of a monocyclic or polycyclic alkyl group in a case in which the alkyl group is a cyclic alkyl group. The substituent alkyl group preferably has 1 to 10 carbon atoms.

The linear or branched substituent alkyl group preferably has 1 to 10 carbon atoms, and examples include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a 1-methylbutyl group, a n-hexyl group, a 2-methylpentyl group, a 3-methylpentyl group, a 2,2-dimethylbutyl group, a 2,3-dimethylbutyl group, a n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, a n-octyl group, an isooctyl group, a 2-ethylhexyl group, a nonyl group, and a decyl group.

The cyclic substituent alkyl group preferably has 3 to 10 carbon atoms, and examples thereof include a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, a 1-adamantyl group, a 2-adamantyl group, and a tricyclodecyl group, and further include such a cyclic alkyl group in which one or more hydrogen atoms are/is substituted with a linear, branched, or cyclic alkyl group. Examples of the linear, branched, or cyclic alkyl group with which hydrogen atom(s) are/is substituted include the same as in the substituent alkyl group.

Examples of the aromatic heterocyclic group as the aromatic group in G include a group obtained by removing two hydrogen atoms each bonding to a carbon atom or a hetero atom included in the ring skeleton, from such each aromatic heterocyclic compound.

Preferable examples of the aromatic heterocyclic compound include a compound having one or more sulfur atoms as atom(s) included in the aromatic heterocyclic skeleton (sulfur-containing aromatic heterocyclic compound), a compound having one or more nitrogen atoms as atom(s) included in the aromatic heterocyclic skeleton (nitrogen-containing aromatic heterocyclic compound), a compound having one or more oxygen atoms as atom(s) included in the aromatic heterocyclic skeleton (oxygen-containing aromatic heterocyclic compound), and a compound having two hetero atoms different from each other, selected from the group consisting of a sulfur atom, a nitrogen atom, and an oxygen atom, as atoms included in the aromatic heterocyclic skeleton.

Examples of the sulfur-containing aromatic heterocyclic compound include thiophene and benzothiophene.

Examples of the nitrogen-containing aromatic heterocyclic compound include pyrrole, imidazole, pyrazole, pyridine, pyrazine, pyrimidine, pyridazine, triazine, indole, isoindole, benzimidazole, purine, indazole, quinoline, isoquinoline, quinoxaline, quinazoline, and cinnoline.

Examples of the oxygen-containing aromatic heterocyclic compound include furan, benzofuran (1-benzofuran), and isobenzofuran (2-benzofuran).

Examples of the compound having two hetero atoms different from each other, included in the aromatic heterocyclic skeleton, include oxazole, isoxazole, thiazole, benzoxazole, benzisoxazole, and benzothiazole.

As atoms included in the ring skeleton of the aromatic heterocyclic group, the atom to which a hydroxyl group is bonding and the atom to which —CH=CH—C(=O)—* is bonding, among atoms included in the ring skeleton of the aromatic heterocyclic group, may be each a carbon atom or a hetero atom, and are preferably each a carbon atom.

The number of hetero atom(s) included in the ring skeleton in the aromatic heterocyclic group is preferably from 1 to 3, and more preferably 1 or 2.

In a case in which the number of hetero atom(s) included in the ring skeleton in the aromatic heterocyclic group is two or more, such hetero atoms may be all the same, may be all different, or may be only partially the same.

Examples of the substituent in the aromatic hydrocarbon group or aromatic heterocyclic group in G include the substituent alkyl group, an alkoxy group, an aryloxy group, a dialkylamino group, a diarylamino group, an alkylarylamino group, an alkylcarbonyl group, an arylcarbonyl group, an alkyloxycarbonyl group, an aryloxycarbonyl group, an alkylcarbonyloxy group, an arylcarbonyloxy group, an alkylthio group, an arylthio group, a cyano group (—CN), a halogen atom, a nitro group, a haloalkyl group (halogenated alkyl group), a hydroxyl group (—OH), a mercapto group (—SH), an amino group, the aromatic hydrocarbon group, and the aromatic heterocyclic group.

The number of such substituent(s) in the aromatic hydrocarbon group or aromatic heterocyclic group in G may be only one, or two or more, and all hydrogen atoms may be each substituted with any of the substituent. The number of such substituent(s) is, for example, preferably from 1 to 4, more preferably from 1 to 3, and still more preferably 1 or 2, depending on the number of hydrogen atoms that can be substituted.

In a case in which the number of such substituents in the aromatic hydrocarbon group or aromatic heterocyclic group is two or more, such substituents may be all the same, may be all different, or may be only partially the same.

Examples of the alkoxy group as the substituent include a monovalent group obtained by bonding the substituent alkyl group to an oxygen atom, for example, a methoxy group, an ethoxy group, a n-propoxy group, an isopropoxy group, or a cyclopropoxy group.

The aryl group bonding to an oxygen atom in the aryloxy group as the substituent may be any of a monocyclic or polycyclic aryl group, and preferably has 6 to 10 carbon atoms. Examples of such an aryl group include a phenyl group, a 1-naphthyl group, a 2-naphthyl group, an o-tolyl group, a m-tolyl group, a p-tolyl group, and a xylyl group (dimethylphenyl group), and further include such an aryl group in which one or more hydrogen atoms are/is substituted with, for example, such an aryl group or the substituent alkyl group. The aryl group having such a substituent preferably has 6 to 10 carbon atoms also including carbon atom(s) of the substituent.

Examples of the dialkylamino group as the substituent include a monovalent group obtained by substituting each of two hydrogen atoms in an amino group (—NH$_2$) with the substituent alkyl group, such as a dimethylamino group or a methylethylamino group. Such two alkyl groups bonding to a nitrogen atom in the dialkylamino group may be the same as or different from each other.

Examples of the diarylamino group as the substituent include a monovalent group obtained by substituting each of two hydrogen atoms in an amino group with the aryl group, such as a diphenylamino group or a phenyl-1-naphthylamino group. Such aryl groups bonding to a nitrogen atom in the diarylamino group may be the same as or different from each other.

Examples of the alkylarylamino group as the substituent include a monovalent group obtained by substituting one hydrogen atom of two hydrogen atoms in an amino group with the substituent alkyl group, and substituting another hydrogen atom thereof with the aryl group, such as a methylphenylamino group.

Examples of the alkylcarbonyl group as the substituent include a monovalent group obtained by bonding the substituent alkyl group to a carbonyl group (—C(=O)—), for example, a methylcarbonyl group (acetyl group).

Examples of the arylcarbonyl group as the substituent include a monovalent group obtained by bonding the aryl group to a carbonyl group, for example, a phenylcarbonyl group (benzoyl group).

Examples of the alkyloxycarbonyl group as the substituent include a monovalent group obtained by bonding the alkoxy group to a carbonyl group, for example, a methyloxycarbonyl group (methoxycarbonyl group).

Examples of the aryloxycarbonyl group as the substituent include a monovalent group obtained by bonding the aryloxy group to a carbonyl group, for example, a phenyloxycarbonyl group (phenoxycarbonyl group).

Examples of the alkylcarbonyloxy group as the substituent include a monovalent group obtained by bonding the substituent alkyl group to a carbon atom of a carbonyloxy group (—C(=O)—O—), for example, a methylcarbonyloxy group.

Examples of the arylcarbonyloxy group as the substituent include a monovalent group obtained by bonding the aryl group to a carbon atom of a carbonyloxy group, for example, a phenylcarbonyloxy group.

Examples of the alkylthio group as the substituent include a monovalent group obtained by bonding the substituent alkyl group to a sulfur atom, for example, a methylthio group, an ethylthio group, a n-propylthio group, an isopropylthio group, or a cyclopropylthio group.

Examples of the arylthio group as the substituent include a monovalent group obtained by bonding the aryl group to a sulfur atom, for example, a phenylthio group, a 1-naphthylthio group, or a 2-naphthylthio group.

Examples of the halogen atom as the substituent include a fluorine atom (—F), a chlorine atom (—Cl), a bromine atom (—Br), and an iodine atom (—I).

Examples of the haloalkyl group as the substituent include a group obtained by substituting one or more hydrogen atoms of the substituent alkyl group with halogen atom(s).

Examples of each halogen atom in the haloalkyl group include those described above, exemplified as halogen atoms serving as substituents.

The number of halogen atom(s) in the haloalkyl group is not particularly limited, and may be one, or two or more. In a case in which the number of halogen atom(s) in the haloalkyl group is two or more, such a plurality of halogen atoms may be all the same, may be all different, or may be only partially the same. The haloalkyl group may be a perhaloalkyl group in which all hydrogen atoms in the alkyl group are each substituted with a halogen atom.

The haloalkyl group is not particularly limited, and examples thereof include a chloromethyl group, a dichloromethyl group, a trichloromethyl group, and a trifluoromethyl group.

In a case in which the substituent in the aromatic hydrocarbon group or aromatic heterocyclic group in G is, for example, an electron-donating group such as an alkoxy group, an aryloxy group, a dialkylamino group, a diarylamino group, an alkylarylamino group, an alkylthio group, or an arylthio group, in the compound (1), wavelength of light necessary for generation of the base by light irradiation becomes longer (make wavelength longer). In other words, the substituent as such an electron-donating group has the advantage of enabling wavelength of light necessary for generation of the base to become longer in the compound (1).

The position of the substituent in the aromatic hydrocarbon group or aromatic heterocyclic group is not particularly limited.

G is preferably an aromatic hydrocarbon group optionally having a substituent, and is more preferably an aromatic hydrocarbon group optionally having one or more substituents in total of one or more kinds selected from the group consisting of an alkoxy group, an aryloxy group, a dialkylamino group, a diarylamino group, an alkylarylamino group, an alkylthio group, and an arylthio group, and examples of such G include a group represented by the following formula (a)-1.

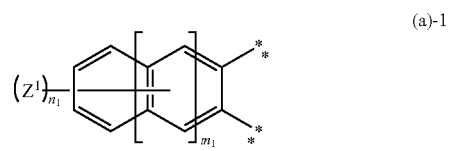

(a)-1

In the formula (a)-1, $m_1$ is an integer of 0 to 2; $n_1$ is an integer of 0 to $2m_1+4$; $Z^1$ is an alkoxy group, an aryloxy group, a dialkylamino group, a diarylamino group, an alkylarylamino group, an alkylthio group, or an arylthio group, and in a case in which $n_1$ is an integer of 2 or more, such a plurality of $Z^1$'s may be the same as or different from each other; and one bond marked with a symbol ** is formed toward the hydroxyl group, as one subject to which G is bonding, and other bond marked therewith is formed toward the carbon atom included in the double bond, as other subject to which G is bonding.

In the formula (a)-1, $m_1$ is an integer of 0 to 2 (0, 1, or 2), and defines the number of ring skeleton(s) included in the aromatic hydrocarbon group. In other words, the aromatic hydrocarbon group in a case in which $m_1$ is 0 is a 1,2-phenylene group, the aromatic hydrocarbon group in a case in which $m_1$ is 1 is a naphthalene-2,3-diyl group, and the aromatic hydrocarbon group in a case in which $m_1$ is 2 is an anthracene-2,3-diyl group.

In the formula (a)-1, $n_1$ is an integer of 0 to $2m_1+4$, and represents the number of bond(s) to the aromatic hydrocarbon group of $Z^1$.

In other words, in a case in which $m_1$ is 0, $n_1$ is an integer of 0 to 4, preferably an integer of 0 to 3, more preferably an integer of 0 to 2, and still more preferably 0 or 1.

In a case in which $m_1$ is 1, $m_1$ is an integer of 0 to 6, preferably an integer of 0 to 4, more preferably an integer of 0 to 3, still more preferably an integer of 0 to 2, and particularly preferably 0 or 1.

In a case in which $m_1$ is 2, $n_1$ is an integer of 0 to 8, preferably an integer of 0 to 4, more preferably an integer of 0 to 3, still more preferably an integer of 0 to 2, and particularly preferably 0 or 1.

In the formula (a)-1, $Z^1$ is an alkoxy group, an aryloxy group, a dialkylamino group, a diarylamino group, an alkylarylamino group, an alkylthio group, or an arylthio group, and is the same as in the substituent included in the aromatic hydrocarbon group or aromatic heterocyclic group in G.

In a case in which $n_1$ is an integer of 2 or more and a plurality of $Z^1$'s are present (the compound (1) has a plurality of $Z^1$'s), such a plurality of $Z^1$'s may be the same as or different from each other. In other words, such $Z^1$'s may be all the same, may be all different, or may be only partially the same.

In a case in which $n_1$ is an integer other than 0, the position of $Z^1$ bonding to the aromatic hydrocarbon group is not particularly limited.

In the formula (a)-1, one bond marked with a symbol  is formed toward the hydroxyl group in the formula (a), as one subject to which G is bonding. Other bond marked with a symbol  is formed toward the carbon atom included in a double bond in the formula (a), as other subject to which G is bonding.

The first skeleton is preferably, for example, a group represented by the following formula (a)-2. The compound including the first skeleton and the second skeleton preferably generates a base in which a hydrogen atom is bonded with the nitrogen atom of the second skeleton by light irradiation, and coumarin or a coumarin derivative.

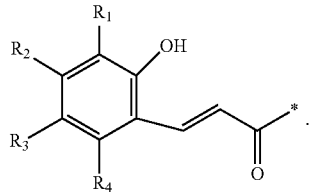

(a)-2

In the formula (a)-2, each of $R_1$ to $R_4$ independently represents a hydrogen atom, the substituent alkyl group, an alkoxy group, an aryloxy group, a dialkylamino group, a diarylamino group, an alkylarylamino group, an alkylcarbonyl group, an arylcarbonyl group, an alkyloxycarbonyl group, an aryloxycarbonyl group, an alkylcarbonyloxy group, an arylcarbonyloxy group, an alkylthio group, an arylthio group, a cyano group (—CN), a halogen atom, a nitro group, a haloalkyl group (halogenated alkyl group), a hydroxyl group (—OH), a mercapto group (—SH), an amino group, the aromatic hydrocarbon group, or the aromatic heterocyclic group, and * represents a bonding position with the nitrogen atom. At least two of $R_1$ to $R_4$ are optionally bonding to each other to form a ring structure.

The second skeleton includes a nitrogen atom bonding to the bonding position of the first skeleton to form an amide group, and a pyridine skeleton in addition to the nitrogen atom. When the base-reactive compound is an epoxy compound, from the point of excellent reactivity when the epoxy compound is irradiated with light and heated, the second skeleton preferably has an aminopyridine skeleton, from the point of further improving the reactivity of the epoxy compound by allowing the terminal portion including the nitrogen atom derived from the amino group of the aminopyridine skeleton to function as a base when a base generated by light irradiation reacts with the epoxy compound, the second skeleton more preferably has a 4-aminopyridine skeleton.

The second skeleton is preferably a group represented by the following formula (C).

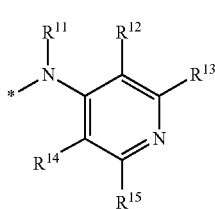

(C)

In the formula (C), $R^{11}$ represents a hydrogen atom, or the substituent alkyl group, each of $R^{12}$ to $R^{15}$ independently represents a hydrogen atom, the substituent alkyl group, an alkoxy group, an aryloxy group, a dialkylamino group, a diarylamino group, an alkylarylamino group, an alkylcarbonyl group, an arylcarbonyl group, an alkyloxycarbonyl group, an aryloxycarbonyl group, an alkylcarbonyloxy group, an arylcarbonyloxy group, an alkylthio group, an arylthio group, a cyano group (—CN), a halogen atom, a nitro group, a haloalkyl group (halogenated alkyl group), a hydroxyl group (—OH), a mercapto group (—SH), an amino group, the aromatic hydrocarbon group, or the aromatic heterocyclic group, and * represents the bonding position with * of the formula (a). At least two of $R^{11}$ to $R^{15}$ are optionally bonding to each other to form a ring structure.

In the formula (C), $R^{11}$ is preferably a hydrogen atom or a methyl group, and from the point of excellent storage stability when preparing a photoreactive composition, more preferably a methyl group. Each of $R^{12}$ to $R^{15}$ is preferably a hydrogen atom, or the substituent alkyl group, and more preferably a hydrogen atom.

(Method of Manufacturing Compound (1))

Hereinafter, one example of a method of manufacturing the compound (1) will be described. As one example of a method of manufacturing the compound (1), a method of manufacturing a compound (compound represented by formula (X-4)), in which the first skeleton is a group represented by the formula (a)-2, and the second skeleton is a group represented by the formula (C), will be described.

At first, a compound in which the hydroxyl group in the group represented by the formula (a)-2 is acetylated and a hydroxyl group is bonded to the bond position (compound represented by formula (X-1)) is prepared.

Next, by substituting OH of the carboxy group in the compound represented by the formula (X-1) with a halogen atom, a compound represented by the formula (X-2) (Y is a halogen atom such a chlorine atom or a bromine atom) is obtained. For example, by reacting the compound (X-1) with thionyl chloride, phosphorus pentachloride or the like, the compound represented by the formula (X-2) can be obtained.

Further, the compound represented by the formula (X-2) is made to react with a compound with the group represented by the formula (C) and with a hydrogen atom bonding to the bonding position. As a result, the halogen atom in the compound represented by the formula (X-2) is substituted with the group represented by the formula (C) to obtain a compound represented by the formula (X-3).

The compound represented by the formula (X-3) is hydrolyzed under a basic condition, thereby allowing the acetyl group to be substituted with a hydroxyl group, and a compound represented by the formula (X-4) is obtained.

The reaction for obtaining the compound represented by the formula (X-4) from the compound represented by the formula (X-1) is as follows.

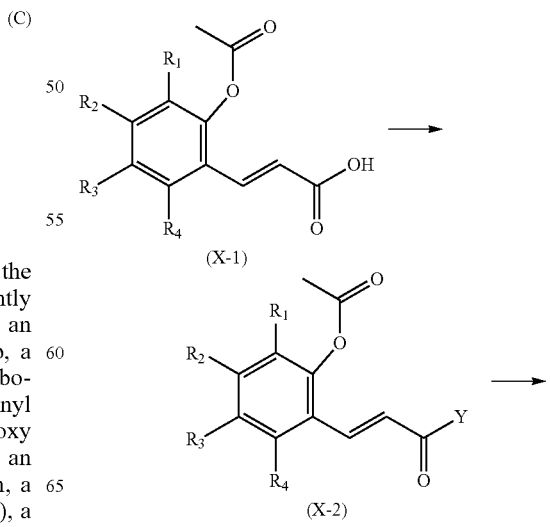

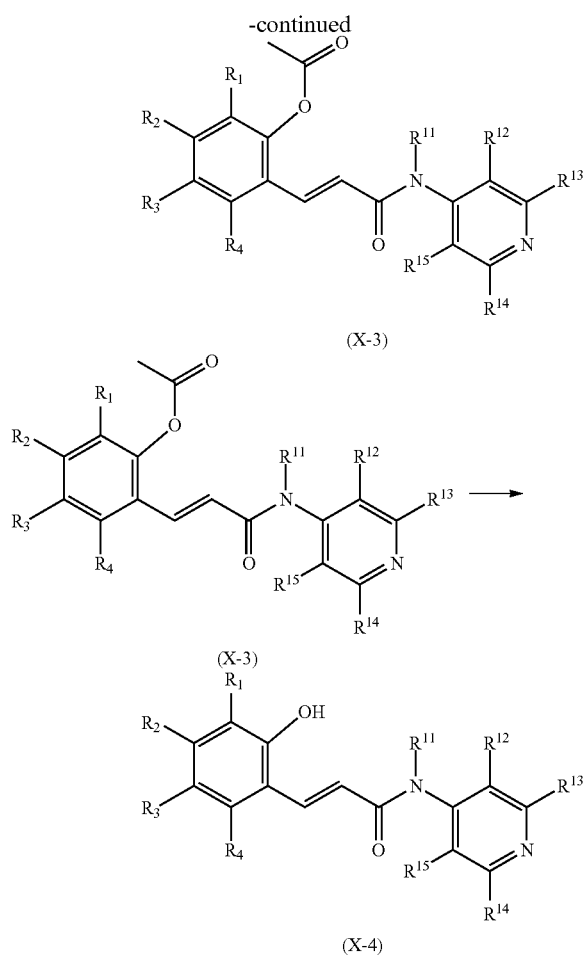

In the formulas (X-1) to (X-4), $R_1$ to $R_4$ are the same as $R_1$ to $R_4$ in the formula (a)-2, and $R^{11}$ to $R^{15}$ are the same as $R^{11}$ to $R^{15}$ in the formula (C) and Y represents a halogen atom.

[Photoreactive Composition]

The photoreactive composition in the present disclosure includes the photobase generator in the present disclosure, and a base-reactive compound, in which the base-reactive compound includes a functional group that is converted, by the action of a base, into a group exhibiting reactivity, or includes a group that reacts in response to the action of a base. The compound including the functional group that is converted, by the action of a base, into the group exhibiting reactivity may be a compound including only one functional group described above, may be a compound including two or more functional groups described above, or may be a mixture thereof. The compound including the group that reacts in response to the action of a base may be a compound including only one group that reacts in response to the action of a base, may be a compound including two or more groups that reacts in response to the action of a base, or may be a mixture thereof.

For example, when the photoreactive composition in the present disclosure is irradiated with light, a base is generated from the photobase generator, and the functional group, which is included in the base-reactive compound of the photoreactive composition, is converted by the action of a base to exhibit reactivity, or the functional group, which is included in the base-reactive compound, reacts by the action of a base. Thus, the aforementioned photoreactive composition is irradiated with light to generate the base, thereby allowing the base-reactive compound included in the photoreactive composition to be reacted, and the reaction product is obtained.

The photoreactive composition may be a photocurable composition that is to be cured by a reaction of a base-reactive compound by light irradiation, and such a photocurable composition may be used for production of a cured product by light irradiation.

The photoreactive composition may be a photoreactive material (positive type) to be solubilized by light irradiation, or may be a photoreactive material (negative type) to be cured by light irradiation.

The photobase generator included in the photoreactive composition of the present disclosure includes, may be adopted singly, or in combination of two or more kinds thereof, and in a case of two or more kinds, the combination and the ratio can be arbitrarily set.

According to the photoreactive composition of the present disclosure, the content ratio of the photo base generator is preferably from 1% by mass to 40% by mass, more preferably from 2% by mass to 35% by mass, and still more preferably from 3% to 10% by mass, with respect to the content ratio of the base-reactive compound. When the content ratio of the photobase generator is 1% by mass or more, the reaction of a base-reactive compound proceeds more easily. When the content of the photobase generator is 40% by mass or less, overuse of the photobase generator is prevented.

(Base-Reactive Compound)

The base-reactive composition in the present disclosure includes the base-reactive compound. The base-reactive compound is the compound (in the present disclosure, also referred to as "base-reactive compound (9-2a)") including the functional group that is converted, by the action of a base, into the group exhibiting reactivity, or the compound (in the present disclosure, also referred to as "base-reactive compound (9-2b)") including the group that reacts in response to the action of a base. The base-reactive compound (9-2b) differs from the base-reactive compound (9-2a) in that the group that reacts is not converted into a group exhibiting reactivity by the action of a base.

Examples of a reaction that proceeds in the base-reactive compound include addition polymerization and condensation polymerization.

For example, the base-reactive compound may be any of a monomer, an oligomer, and a polymer, or may be either of a low molecular compound or a high molecular compound.

As the base-reactive compound, the known compound can be used, and for example, the base-reactive compounds described in "Japanese Patent Application Laid-Open (JP-A) No. 2011-80032" can be used. However, these compounds are just an example.

Examples of the base-reactive compound (9-2a) include a compound in which the functional group is decomposed by the action of a base and converted into a group exhibiting reactivity. Examples of such a base-reactive compound (9-2a) include a compound including a carbonate skeleton (—O—C(=O)—O—), and a photosensitive polyimide.

Examples of the base-reactive compound (9-2b) include an epoxy compound, a silicone resin, an alkoxysilane compound, a (meth)acrylate compound, a thiol compound.

In the disclosure, "(meth)acrylate" is a concept that includes both "acrylate" and "methacrylate".

The base-reactive compound included in the photoreactive composition of the present disclosure, may be adopted singly, or in combination of two or more kinds thereof, and in a case of two or more kinds, the combination and the ratio can be arbitrarily set.

The content ratio of the base-reactive compound in the photoreactive composition of the present disclosure is preferably from 40% by mass to 90% by mass, and more preferably from 45% by mass to 80% by mass with respect to the total of amount of non-volatile content of the photoreactive composition.

<Epoxy Compound>

The photoreactive composition of the present disclosure preferably includes an epoxy compound as the base-reactive compound. The epoxy compound may include an epoxy compound having one or more epoxy groups in one molecule, and preferably includes an epoxy compound having two or more epoxy groups. The epoxy compound can be arbitrarily selected depending on the purpose.

The epoxy compound may be, for example, any of a monomer, an oligomer and a polymer, and may be any of a small molecule compound and a polymer compound.

The photoreactive composition of the present disclosure includes an epoxy compound, thereby when the photoreactive composition is irradiated with light and heated, allowing the reactivity of the epoxy compound at a relatively low heating temperature (for example, 120° C. or lower) to be excellent.

The epoxy compound is not particularly limited, and examples thereof include diglycidyl ether, ethylene glycol diglycidyl ether, glycerin diglycidyl ether, propylene glycol diglycidyl ether, butanediol diglycidyl ether, diethylene glycol diglycidyl ether, glycerol polyglycidyl ether, diglycerol polyglycidyl ether, sorbitol polyglycidyl ether, allyl glycidyl ether, butyl glycidyl ether, phenyl glycidyl ether, alkylphenol glycidyl ether, polyethylene glycol diglycidyl ether, tripropylene glycol diglycidyl ether, neopentyl glycol diglycidyl ether, 1,6-hexanediol diglycidyl ether, glycerin polyglycidyl ether, diglycerin polyglycidyl ether, trimethylolpropane polyglycidyl ether, cresyl glycidyl ether, aliphatic diglycidyl ether, polyfunctional glycidyl ether, tertiary fatty acid monoglycidyl ether, spiroglycol diglycidyl ether, glycidyl propoxytrimethoxysilane, 3, 4-epoxycyclohexylmethyl-3,4-epoxycyclohexanecarboxylate, bisphenol A diglycidyl ether, and bisphenol F diglycidyl ether. These epoxy compounds may be halogenated or hydrogenated.

(Other Component)

The photoreactive composition of the present disclosure may further include any component other than the base-reactive compound, and the photobase generator.

Such other component is not particularly limited and can be arbitrarily selected for any purpose, as long as the effect of the invention is not impaired.

Such other component included in the photoreactive composition may be adopted singly, or in combination of two or more kinds thereof, and in a case of two or more kinds, the combination and the ratio can be arbitrarily set.

Examples of such other component include sensitizers, fillers, pigments, and solvents.

<Sensitizer>

The photoreactive composition of the present disclosure may include a sensitizer.

The sensitizer is not particularly limited and examples thereof include benzophenone, naphthoquinone, anthraquinone, xanthene, thioxanthene, xanthone, thioxanthone, anthracene, phenanthrene, phenanthroline, pyrene, pentacene, and derivatives thereof.

The sensitizer may be adopted singly, or in combination of two or more kinds thereof, and in a case of two or more kinds, the combination and the ratio can be arbitrarily set.

The content of the sensitizer in the photoreactive composition is not particularly limited and may be appropriately modulated.

<Filler>

The photoreactive composition in the present disclosure may include a filler. A filler can be included, thereby allowing characteristics, for example, the viscosity of the photoreactive composition itself, and the strength of the photoreactive composition (reaction product described below) after the reaction to be modulated.

The filler may be any known filler and is not particularly limited. For example, the filler may be any of a fibrous, plate-like, or granular filler, and the shape, the size, and the material thereof may be each appropriately selected for any purpose.

The filler included in the photoreactive composition may be adopted singly, or in combination of two or more kinds thereof, and in a case of two or more kinds, the combination and the ratio can be arbitrarily set.

The content of the filler in the photoreactive composition is not particularly limited and may be appropriately modulated for any purpose.

<Pigment>

The photoreactive composition in the present disclosure may include a pigment. A pigment can be included, thereby allowing, for example, light permeability to be modulated.

The pigment included in the photoreactive composition may be any known pigment such as a white, blue, red, yellow, or green pigment, and is not particularly limited.

The pigment included in the photoreactive composition may be adopted singly, or in combination of two or more kinds thereof, and in a case of two or more kinds, the combination and the ratio can be arbitrarily set.

The content of the pigment in the photoreactive composition is not particularly limited and may be appropriately modulated for any purpose.

<Solvent>

The photoreactive composition in the present disclosure may include a solvent. A solvent can be included, thereby allowing handleability to be enhanced.

The solvent is not particularly limited, and may be appropriately selected in consideration of solubility, stability, and the like of the base-reactive compound and the photobase generator.

The solvent is not particularly limited, and examples thereof include halogenated hydrocarbon such as dichloromethane or chloroform; aromatic hydrocarbon such as toluene, o-xylene, m-xylene, or p-xylene; aliphatic hydrocarbon such as hexane, heptane, or octane; carboxylate ester such as ethyl acetate or butyl acetate; ether such as diethyl ether, tetrahydrofuran (THF), or 1,2-dimethoxyethane (dimethylcellosolve); ketone such as acetone, methyl ethyl ketone (MEK), cyclohexanone, or cyclopentanone; nitrile such as acetonitrile; and amide such as N,N-dimethylformamide (DMF) or N,N-dimethylacetamide.

The solvent included in the photoreactive composition may be adopted singly, or in combination of two or more kinds thereof, and in a case of two or more kinds, the combination and the ratio can be arbitrarily set.

The content of the solvent in the photoreactive composition is preferably from 3 times by mass to 20 times by mass, more preferably from 4 times by mass to 15 times by mass, and still more preferably from 5 times by mass to 10 times by mass with respect to the content of the base-reactive compound. The content of the solvent is in such a range, thereby allowing the photoreactive composition to be more enhanced in handleability.

The photoreactive composition is obtained by blending the base-reactive compound, the photobase generator, and, if necessary, any other component. One obtained after blending of such respective components may be adopted as the photoreactive composition as it is, or may be, if necessary, subsequently subjected to, for example, a known purification operation, thereby obtaining the photoreactive composition.

The blending of such respective components may be performed by adding all the components and then mixing them, performing mixing while sequentially adding some of the components, or performing mixing while sequentially adding all the components.

The mixing method is not particularly limited, and may be appropriately selected from known methods including a method involving mixing under rotation of, for example, a stirring bar or a stirring blade; a method involving mixing by use of, for example, a mixer; and a method involving mixing by addition of ultrasonic wave.

The temperature in the blending is not particularly limited as long as the respective components blended are not degraded, and the temperature can be, for example, from 3° C. to 30° C.

The blending time is also not particularly limited as long as the respective components blended are not degraded, and the time can be, for example, from 30 seconds to 1 hour.

It is noted that these blending conditions are merely examples.

<Reaction Product>

The reaction product in the present disclosure is obtained by reacting the photoreactive composition. The method of producing the reaction product in the present disclosure is described in the section of the method of producing a reaction product in the disclosure, described below.

The shape of the reaction product in the present disclosure is, for example, a film or a rod shape, and can be arbitrarily selected for any purpose.

(Method of Producing Reaction Product)

The method of producing a reaction product in the disclosure includes a step of irradiating the photoreactive composition with light, thereby generating a base from the photobase generator. the functional group, which is included in the base-reactive compound, reacts by the action of a base generated. Thus, because the aforementioned photoreactive composition is irradiated with light to generate the base, the base-reactive compound included in the photoreactive composition is reacted, and the reaction product is obtained.

The photoreactive composition may be attached to an objective substance according to a known procedure, and then, if necessary, pre-baked (for example, dried), thereby forming a photoreactive composition layer, and the photoreactive composition layer may be irradiated with light.

For example, in a case in which a film-like reaction product is produced, the reaction product may be produced by coating an objective substance with the photoreactive composition by use of any of various coaters such as a spin coater, an air knife coater, a blade coater, a bar coater, a gravure coater, a roll coater, a roll knife coater, a curtain coater, a die coater, a knife coater, a screen coater, a meyer bar coater, and a kiss coater, or a coating unit such as an applicator, or dipping an objective substance in the photoreactive composition, thereby allowing the photoreactive composition to be attached to the objective substance.

For example, in a case in which a film-like or rod-like reaction product is produced, the reaction product may be produced by allowing the photoreactive composition to be attached to an objective substance by use of a printing method such as a screen printing method, a flexographic printing method, an offset printing method, an inkjet printing method, a dispenser printing method, a jet dispenser printing method, a gravure printing method, a gravure offset printing method, or a pad printing method.

The pre-baking may be performed in conditions of, for example, from 40° C. to 120° C. and from 30 seconds to 10 minutes, and is not particularly limited.

The wavelength of light with which the photoreactive composition is irradiated is not particularly limited, and may be, for example, any wavelength in the ultraviolet to visible region. The wavelength of light with which the photoreactive composition is irradiated may be 10 nm or more, may be 200 nm or more, or may be 300 nm or more. The wavelength of light with which the photoreactive composition is irradiated may be 600 nm or less, may be 500 nm or less, or may be 400 nm or less.

The illuminance of light with which the photoreactive composition is irradiated is, for example, preferably from 1 mW/cm$^2$ to 100 mW/cm$^2$, more preferably from 5 mW/cm$^2$ to 80 mW/cm$^2$, and still more preferably from 10 mW/cm$^2$ to 60 mW/cm$^2$.

The exposure doses with which the photoreactive composition is irradiated is, for example, preferably from 100 mJ/cm$^2$ to 20000 mJ/cm$^2$, more preferably from 200 mJ/cm$^2$ to 15000 mJ/cm$^2$, and still more preferably from 300 mJ/cm$^2$ to 12000 mJ/cm$^2$.

It is noted that light irradiation conditions here listed are merely examples and are not limited thereto.

Such a reaction product obtained by irradiating the photoreactive composition with light may be further subjected to post-baking (heating treatment after light irradiation).

The post-baking may be performed in conditions of, for example, from 50° C. to 180° C. and from 20 minutes to 2 hours, in case in which an epoxy compound is used as the base-reactive compound, may be preferably performed in condition of from 70° C. to 140° C. and from 20 minutes to 2 hours, may be more preferably performed in condition of from 90° C. to 120° C. and from 20 minutes to 2 hours, or may be still more preferably performed in condition of from 90° C. to 100° C. and from 20 minutes to 2 hours.

The thickness of the reaction product may be appropriately set for any purpose, and is not particularly limited. The thickness of the reaction product is, for example, preferably from 1 μm to 500 μm, and more preferably from 5 μm to 200 μm. A reaction product having such a thickness can be formed by, for example, setting the thickness of the photoreactive composition layer to any thickness equal to or more than the thickness of an objective reaction product.

For example, the ratio of the thickness of the reaction product (thickness of photoreactive composition layer after light irradiation) with respect to the thickness of the photoreactive composition layer (thickness of photoreactive composition layer before light irradiation) ([thickness of photoreactive composition layer after light irradiation]/[thickness of photoreactive composition layer before light irradiation]) can be, for example, from 0.2 to 1.0, and can be any of from 0.3 to 1.0, from 0.4 to 1.0, from 0.5 to 1.0, from 0.6 to 1.0, from 0.7 to 1.0, from 0.8 to 1.0, or from 0.9 to 1.0, by further modulation of reaction conditions.

EXAMPLES

Hereinafter, the invention will be more specifically described with reference to Examples, but the invention is not limited by these Examples.

<Production of Compound (1)-1>

At first, as shown below, a compound (X) was reacted with thionyl chloride and 4-aminopyridine in this order to produce a compound (Y).

In practice, after stirring a liquid mixture of the compound (X) (1.2 g, 0.0055 mol) and thionyl chloride (SOCl$_2$, 10 mL) at room temperature for 10 hours, dry tetrahydrofuran (20 mL), and a liquid mixture of 4-aminopyridine (1.3 g, 0.012 mol) and dry tetrahydrofuran (50 mL) were respectively added to this liquid mixture, and the thus-obtained liquid mixture was stirred at 0° C. for 12 hours to perform the reaction.

Next, a saturated sodium chloride aqueous solution was added to the reaction liquid, and then the reaction liquid was washed by shaking in a separating funnel. The washing with this saturated sodium chloride aqueous solution was performed once more, and a total of twice.

As a result, the compound (Y) was obtained.

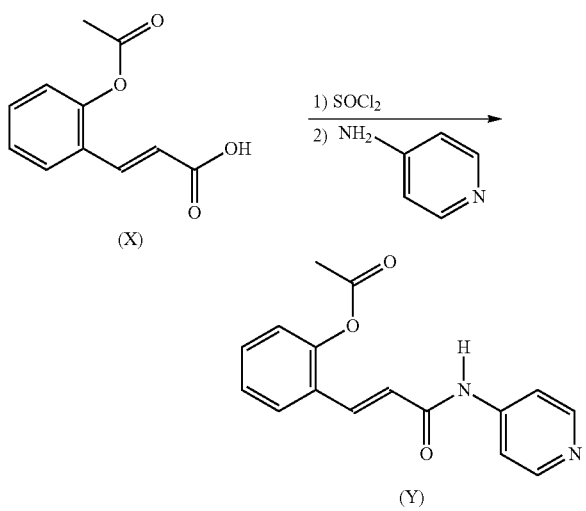

Next, the compound (Y) was hydrolyzed by the reaction shown below to produce compound (1)-1.

In practice, a mixture of a saturated aqueous potassium carbonate solution (20 mL) was added to a mixture in which methanol (30 mL) is mixed with the compound (Y) obtained as described above, and the reaction was performed by heating and stirring the thus obtained mixture for 20 hours. After completion of the reaction, 35% by mass hydrochloric acid was added to the reaction liquid.

Next, the obtained reaction liquid was filtered to obtain the objective compound (1)-1 as a yellow solid (yield 66%).

Regarding the obtained compound (1)-1, the analysis results of $^1$H-NMR, 13C-NMR, and ESI-MS are shown in Table 1.

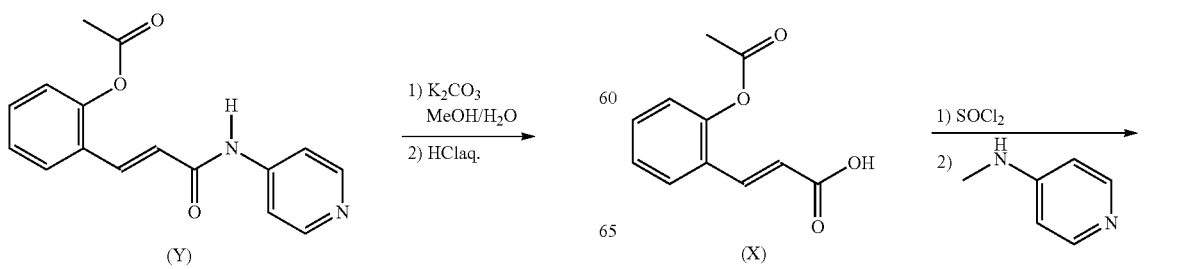

TABLE 1

| | |
|---|---|
| $^1$H-NMR [δ/ppm] (DMSO-d$_6$, 300 MHz) | 6.8-7.0 (m, 2H, Ar—H)<br>6.93 (d, 1H, J = 15 Hz, —CH=CHCO)<br>7.2-7.5 (m, 2H, Ar—H)<br>7.67 (dd, 2H, J = 1.5, 6.3 Hz, Py-H)<br>7.83 (d, 1H, J = 15 Hz, —CH=CHCO—)<br>8.44 (dd, 2H, J = 1.5, 6.3 Hz, Py-H)<br>10.3 (br, 1H, —OH)<br>10.5 (s, 1H, —NH) |
| $^{13}$C-NMR [δ/ppm] (DMSO-d$_6$, 75 MHz) | 113, 116, 119, 121, 121, 129, 131, 138, 146, 150, 157 (sp$^2$), 165 (C=O) |
| ESI-Positive-HR [M + Na]$^+$ | Measured value: 263.07938<br>Calculated value: 263.07965<br>(Estimated composition formula: C$_{14}$H$_{12}$N$_2$Na$_1$O$_2$)<br>Mass difference: −0.27 mmu |

Moreover, the solubility of the compound (1)-1 in the solvent was confirmed. Specifically, the amount of the solvent required to dissolve 10 mg of the compound (1)-1 was confirmed for each solvent. The amount of the solvent required was from 1 mL to 5 mL when tetrahydrofuran or acetone was used, and 1 mL or less when cyclopentanone, methanol or dimethyl sulfoxide was used.

<Production of Compound (1)-2>

At first, as shown below, the compound (X) was reacted with thionyl chloride and 4-methylaminopyridine in this order to produce a compound (Z).

In practice, after stirring a liquid mixture of the compound (X) (2.1 g, 0.010 mol) and thionyl chloride (SOCl$_2$, 10 mL) at room temperature for 10 hours, dry tetrahydrofuran (30 mL), and a liquid mixture of 4-methylaminopyridine (2.3 g, 0.022 mol) and dry tetrahydrofuran (40 mL) were respectively added to this liquid mixture, and the thus-obtained liquid mixture was stirred at 0° C. for 12 hours to perform the reaction.

Next, a saturated sodium chloride aqueous solution was added to the reaction liquid, and then the reaction liquid was washed by shaking in a separating funnel. The washing with this saturated sodium chloride aqueous solution was performed once more, and a total of twice.

As a result, the compound (Z) was obtained.

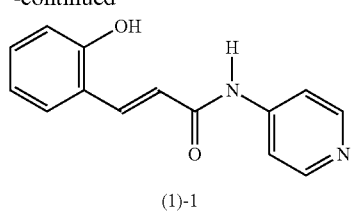

-continued

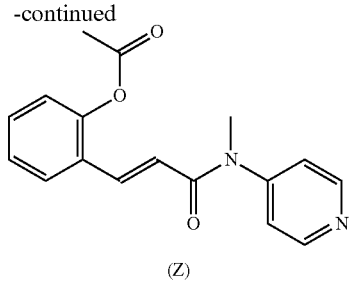
(Z)

Next, the compound (Z) was hydrolyzed by the reaction shown below to produce compound (1)-2.

In practice, a mixture of a saturated aqueous potassium carbonate solution (20 mL) was added to a mixture in which methanol (30 mL) is mixed with the compound (Z) obtained as described above, and the reaction was performed by heating and stirring the thus obtained mixture for 20 hours. After completion of the reaction, 35% by mass hydrochloric acid was added to the reaction liquid.

Next, the obtained reaction liquid was purified by silica gel column chromatography using a mixed solvent of chloroform/methanol (14/1, volume ratio) as the mobile phase, and by collecting and concentrating the fractions including the objective substance, the objective compound (1)-2 was obtained as a light yellow solid (yield 7.1%)

Regarding the obtained compound (1)-2, the analysis results of $^1$H-NMR, $^{13}$C-NMR, and ESI-MS are shown in Table 2.

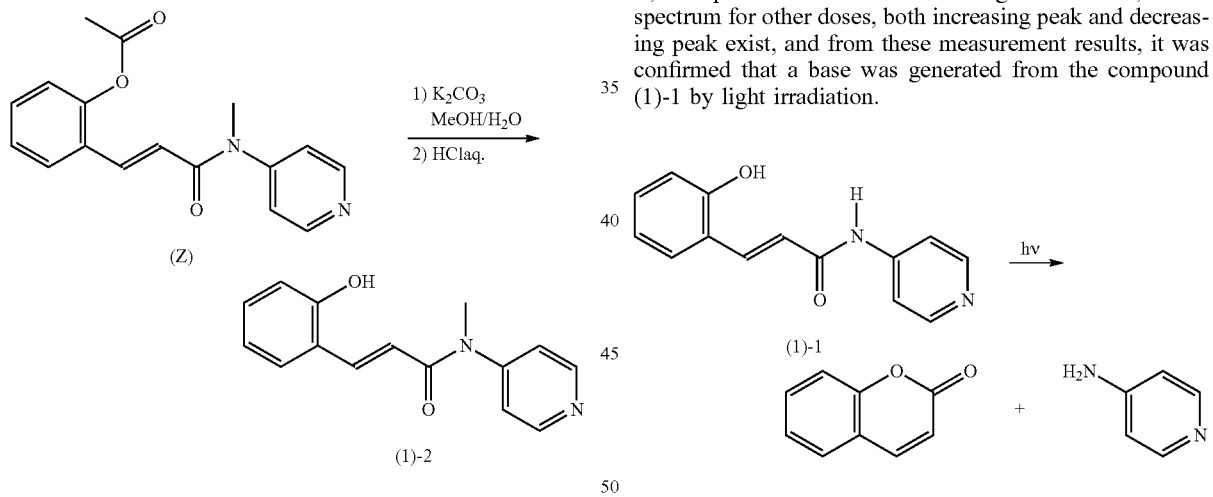

TABLE 2

| 1H-NMR [δ/ppm] (DMSO-d$_6$, 300 MHz) | 3.35 (s, 3H, —NCH$_3$—) |
| --- | --- |
| | 6.8-7.0 (m, 2H, Ar—H) |
| | 6.93 (d, 1H, J = 15 Hz, —C$\underline{H}$=CHCO) |
| | 7.2-7.5 (m, 2H, Ar—H) |
| | 7.67 (dd, 2H, J = 1.5, 6.3 Hz, Py-H) |
| | 7.83 (d, 1H, J = 15 Hz, -CH=C$\underline{H}$CO—) |
| | 8.44 (dd, 2H, J = 1.5, 6.3 Hz, Py-H) |
| | 10.3 (br, 1H, —OH) |
| $^{13}$C-NMR [δ/ppm] (DMSO-d$_6$, 300 MHz) | 36 (sp$^3$), 116, 118, 119, 121, 121, 121, 129, 131, 138, 151, 157 (sp$^2$), 166 (C=O) |
| ESI-Positive-HR [M + H]$^+$ | Calculated value: 277.09530 |
| | Measured value: 277.09456 |
| | (Estimated composition formula: C$_{15}$H$_{14}$N$_2$Na$_1$O$_2$) |
| | Mass difference: −0.73 mmu |

Test Example 1

(Confirmation of Behavior of Compound (1)-1 in Solvent Under Light Irradiation with Wavelength of 313 nm)

The compound (1)-1 obtained above was dissolved in methanol so as to have a concentration of $2.0 \times 10^{-5}$ mol/L. Then, using a mercury xenon lamp, the illuminance was set to 5 mW/cm$^2$, the exposure doses were set to 0, 10, 30, 60 and 100 mJ/cm$^2$, and the obtained methanol solution was irradiated with light having a wavelength of 313 nm. Then, the absorbance of the compound (1)-1 was measured. The result is shown in FIG. 1.

Test Example 2

(Confirmation of Behavior of Compound (1)-1 in Solvent Under Light Irradiation with Wavelength of 365 nm)

The compound (1)-1 obtained above was dissolved in methanol so as to have a concentration of $2.0 \times 10^{-5}$ mol/L. Then, using an LED lamp, the illuminance was set to 10 mW/cm$^2$, the exposure doses were set to 0, 10, 30, 60 and 100 mJ/cm$^2$, and the obtained methanol solution was irradiated with light having a wavelength of 365 nm. Then, the absorbance of the compound (1)-1 was measured. The result is shown in FIG. 2.

In Test Example 1, the molar absorption coefficient was $\varepsilon_{313} = 2.3 \times 10^4$ L/(mol·cm), and in Test Example 2, the molar absorption coefficient was $\varepsilon_{365} = 6.9 \times 10^3$ L/(mol·cm).

Figure 2:
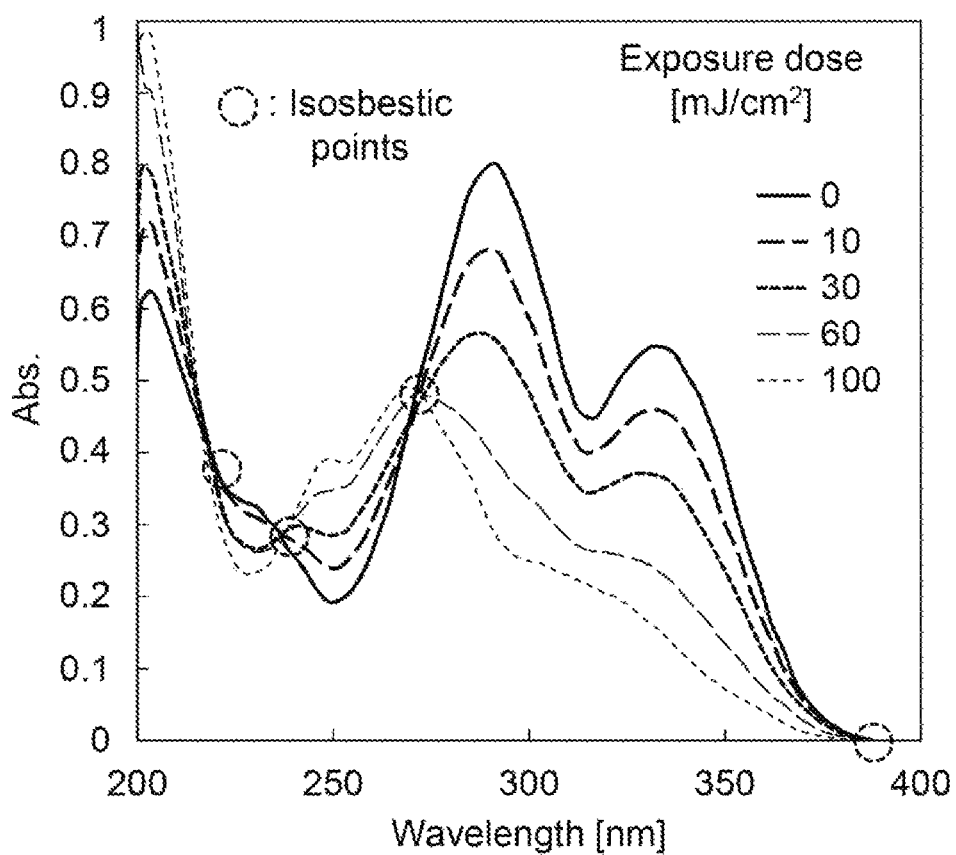
FIG. 2 is data that illustrates the measurement results of the absorbance of the compound (1)-1 in Test Example 2.

As is clear from FIG. 1 and FIG. 2, as compared with the spectrum in the case of the exposure doses of 0 mJ/cm$^2$, that is, the spectrum in the case of no light irradiation, in the spectrum for other doses, both increasing peak and decreasing peak exist, and from these measurement results, it was confirmed that a base was generated from the compound (1)-1 by light irradiation.

Test Example 3

(Confirmation of Behavior of Compound (1)-1 in Polymer Solid Under Light Irradiation)

Polytetramethylene glycol (0.13 g), compound (1)-1 (0.035 g, 26% by mass with respect to polytetramethylene glycol), and tetrahydrofuran (0.54 g) were blended and stirred at 25° C. for 1 minute to obtain a resin composition for the test.

Figure 3:
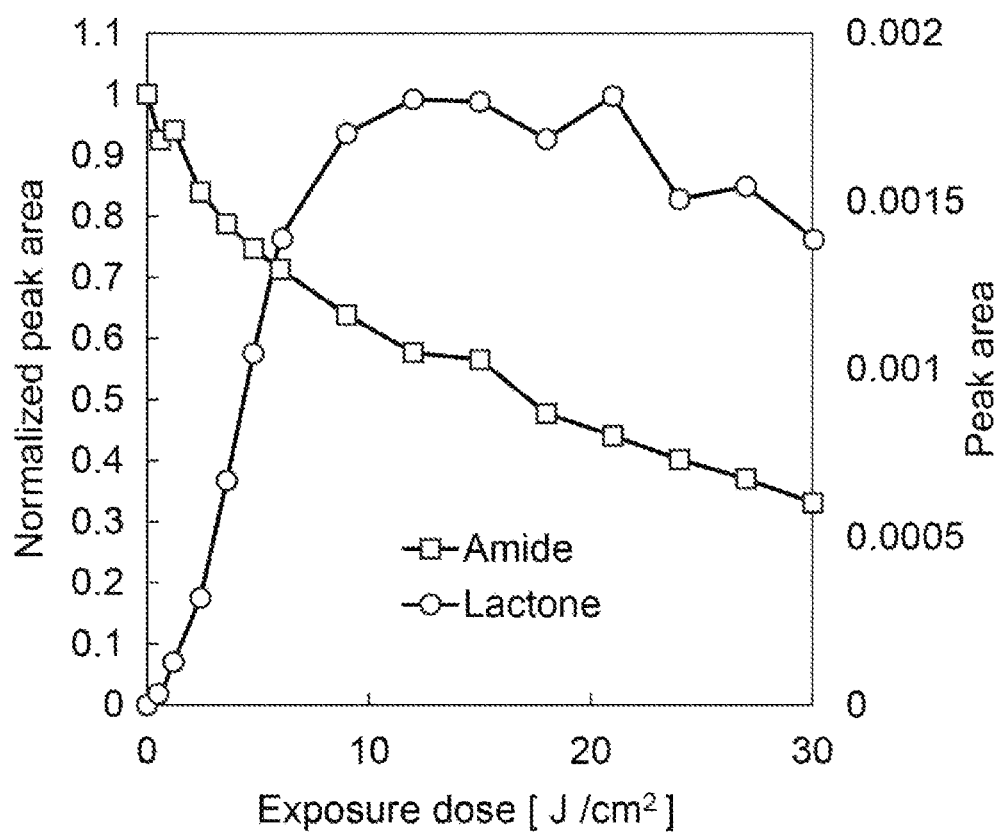
FIG. 3 is a graph illustrating the relationship between the exposure doses to the compound (1)-1 and the peak areas of an amide group and a lactone structure in IR spectra in Test Example 3.

Next, the resin composition for the test was applied onto a calcium fluoride plate by a spin coating method under the conditions of 500 rpm and 10 seconds, the thus-obtained coating film was heated at 60° C. for 3 minutes, and then using a low pressure mercury lamp, the illuminance was set to 12 mW/cm$^2$, and the coating film was irradiated with light having a wavelength of 313 nm. At this time, in the exposure doses of 0 mJ/cm² to 30,000 mJ/cm², the peak intensity derived from an amide group and the peak intensity derived from a lactone structure were measured with a Fourier transform infrared spectrophotometer (FT-IR). The relationship between the exposure doses to the compound (1)-1 and the peak areas of an amide group and a lactone structure in IR spectra is shown in FIG. 3.

Test Example 4

(Confirmation of Behavior of Compound (1)-1 in Polymer Solid Under Light Irradiation)

The same experiment as in Test Example 3 was performed except that an LED lamp was used instead of a mercury xenon lamp, and the illuminance was set to 50 mW/cm², and the coating film was irradiated with light having a wavelength of 365 nm. The relationship between the exposure doses to the compound (1)-1 and the peak areas of an amide group and a lactone structure in IR spectra is shown in FIG. 4.

Figure 4:
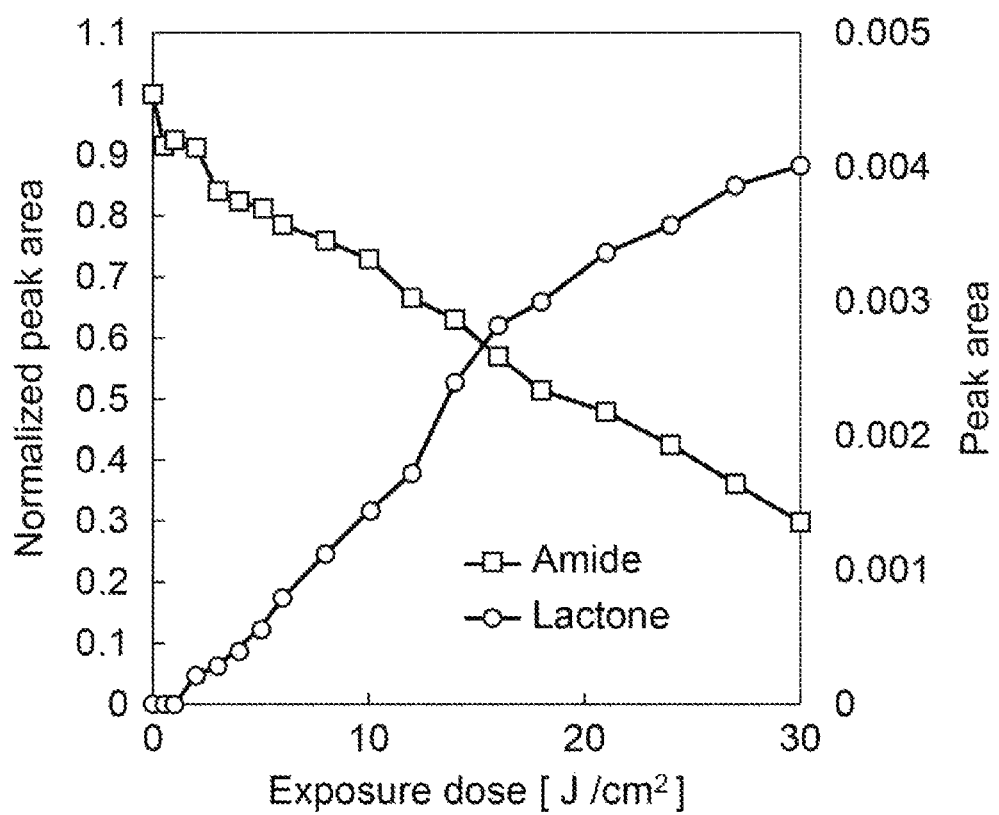
FIG. 4 is a graph illustrating the relationship between the exposure doses to the compound (1)-1 and the peak areas of an amide group and a lactone structure in IR spectra in Test Example 4.

As is clear from FIG. 3 and FIG. 4, as the exposure doses increased, there was a tendency that the peak intensity derived from an amide group decreased and the peak intensity derived from a lactone structure increased. From this, it was confirmed that a base was generated from the compound (1)-1 in the reaction shown below by light irradiation.

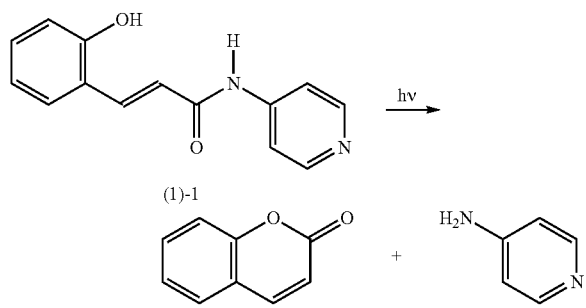

Test Example 5

(UV Curing of Liquid Epoxy Compound Using Compound (1)-1)

At first, a glycidylamine-type epoxy compound (0.21 g, hereinafter also referred to as "NN"), which is a liquid epoxy compound showing the structure below, and the compound (1)-1 (0.0030 g, 0.0062 g, 0.012 g, respectively, 2.5 mol %, 5 mol %, 10 mol % with respect to NN) and cyclopentanone (respectively, 0.67 g, 0.72 g, 0.69 g with respect to 0.030 g, 0.0062 g, 0.012 g of compound (1)-1) were blended and stirred at 25° C. for 1 minute to obtain a photoreactive composition.

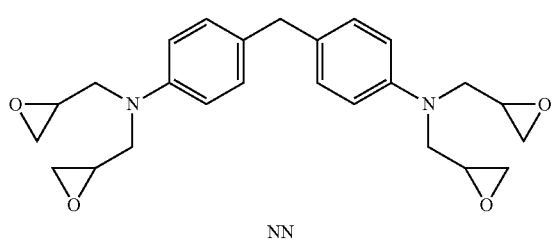 [SMILES: c1cc(N(CC2CO2)CC2CO2)ccc1Cc1ccc(N(CC2CO2)CC2CO2)cc1 ; "NN"]

NN

The photoreactive composition obtained above was applied onto a silicon wafer by a spin coating method under the conditions of 1500 rpm and 10 seconds. Next, after heating (pre-baking) this coating film (photoreactive composition layer) at 60° C. for 3 minutes, the illuminance is set to 50 mW/cm² and the coating film is irradiated with light having a wavelength of 365 nm using an LED lamp. Three types of coating films with the exposure doses of 0 mJ/cm² (unirradiated), 1000 mJ/cm², 5000 mJ/cm² and 10000 mJ/cm² were prepared respectively, and after light irradiation, they were heated (post-baked) at 80° C., 100° C. or 120° C. for 60 minutes, respectively. From the above, it was attempted to finally make each of the coating films into a reaction product obtained by polymerizing NN, which is an epoxy compound.

Figure 5:
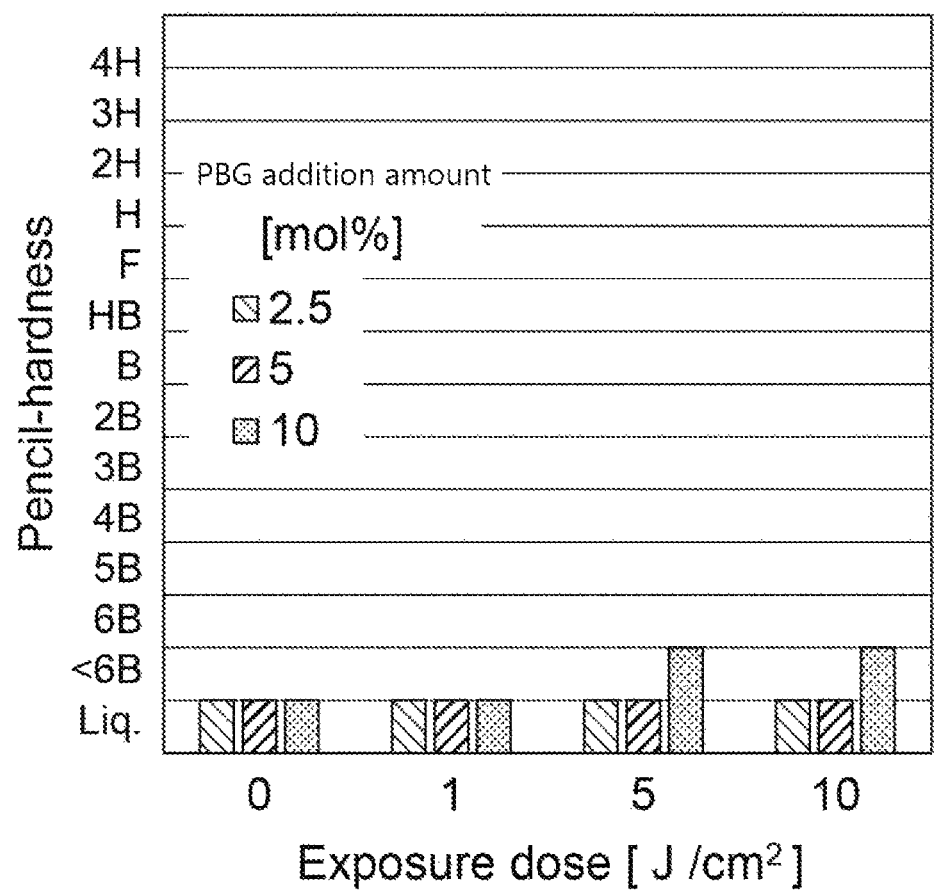
FIG. 5 is a graph illustrating the relationship between the exposure doses and the pencil-hardness of the reaction product after heating the coating film after light irradiation at 80° C. for 60 minutes in Test Example 5.
Figure 6:
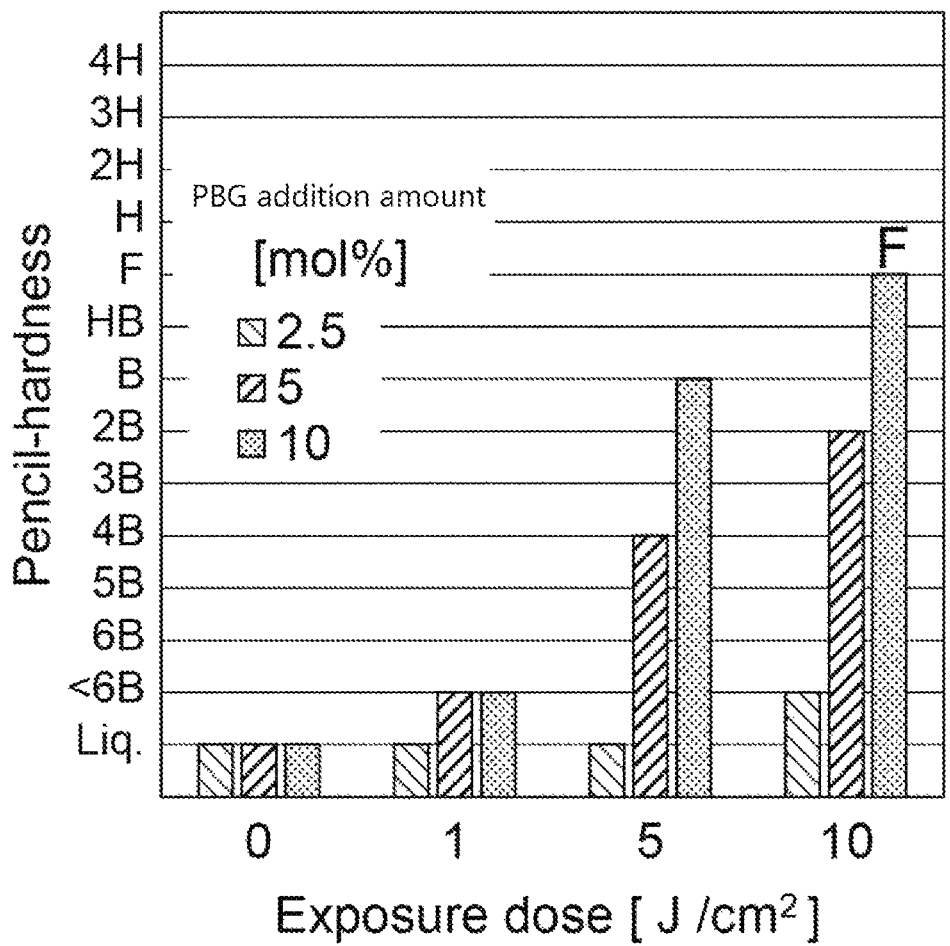
FIG. 6 is a graph illustrating the relationship between the exposure doses and the pencil-hardness of the reaction product after heating the coating film after light irradiation at 100° C. for 60 minutes in Test Example 5.
Figure 7:
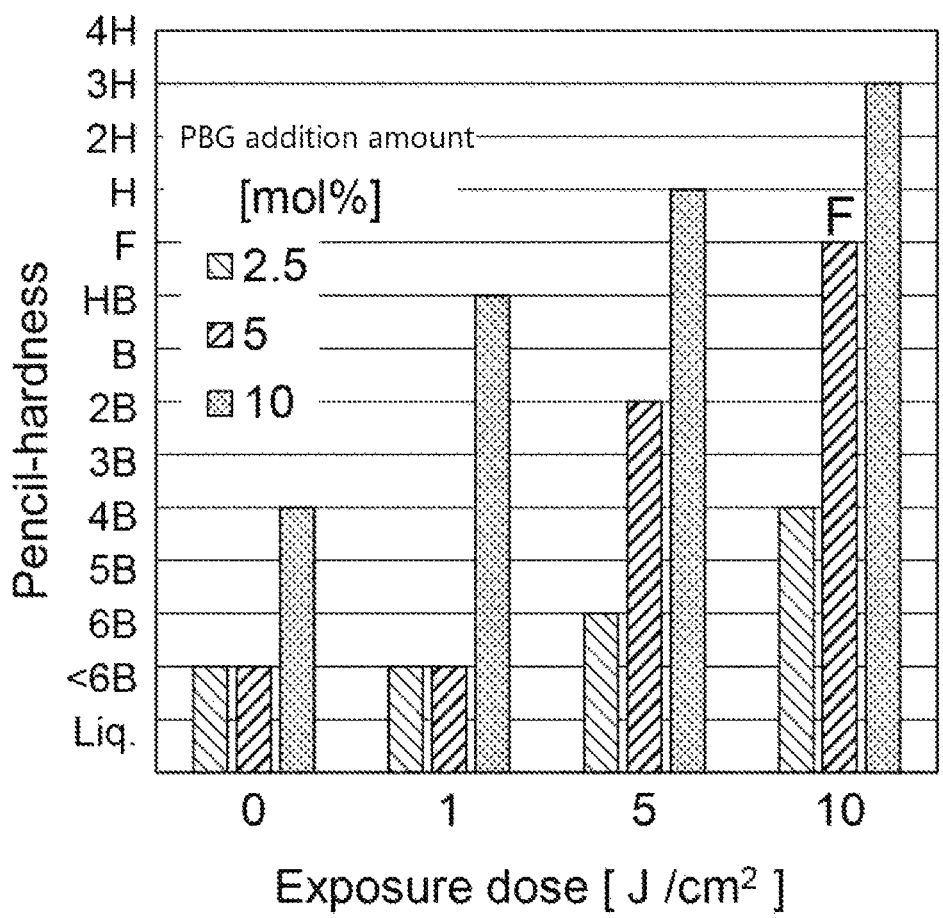
FIG. 7 is a graph illustrating the relationship between the exposure doses and the pencil-hardness of the reaction product after heating the coating film after light irradiation at 120° C. for 60 minutes in Test Example 5.

Coating films in which the exposure doses were set to 0 mJ/cm² (unirradiated), 1000 mJ/cm² (1 J/cm²), 5000 mJ/cm² (5 J/cm²) and 10000 mJ/cm² (10 J/cm²) were heated at 80° C., 100° C. or 120° C. for 60 minutes to obtain reaction products and the pencil-hardness of thus obtained reaction products was determined. The results are shown in FIGS. 5 to 7 (PBG in the figure means compound (1)-1). As shown in FIGS. 5 to 7, it was possible to cure the liquid epoxy compound by UV irradiation at a low temperature of 120° C. or lower without using a curing accelerator such as an imidazole compound.

Figure 8:
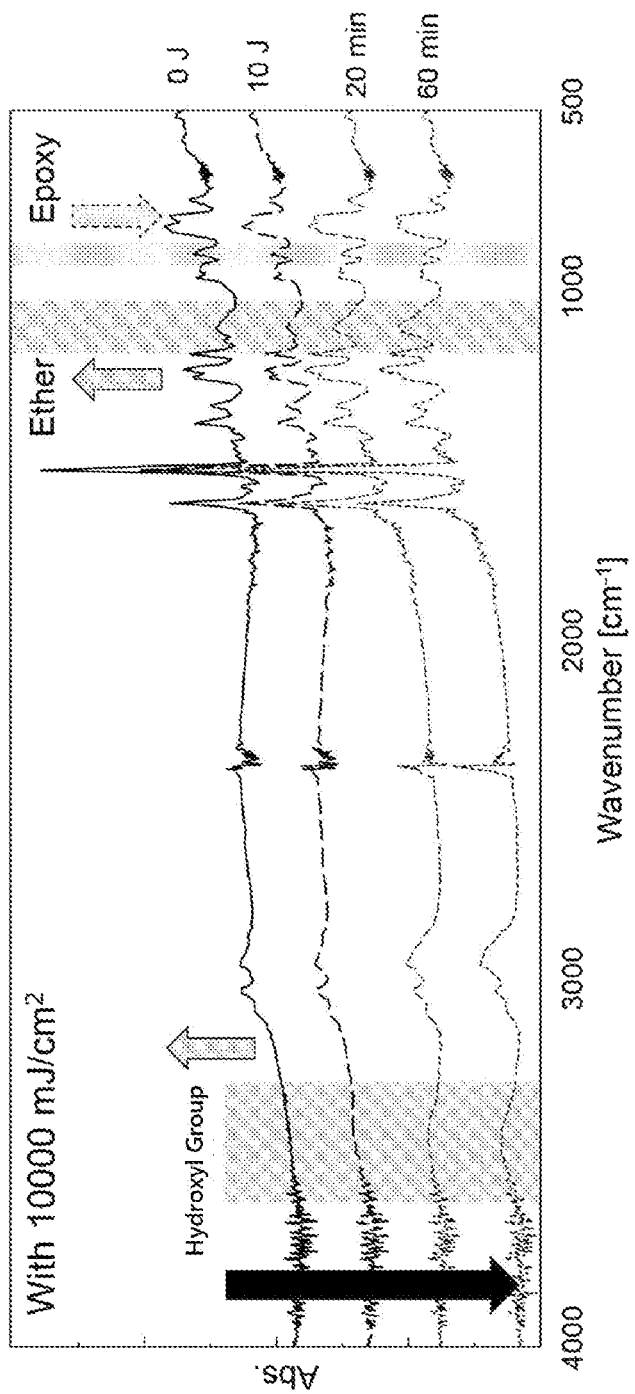
FIG. 8 is a result measuring absorption spectra with a Fourier transform infrared spectrophotometer (FT-IR) under the condition that the coating film was heated at 120° C. after light irradiation to obtain a reaction product.
Figure 9:
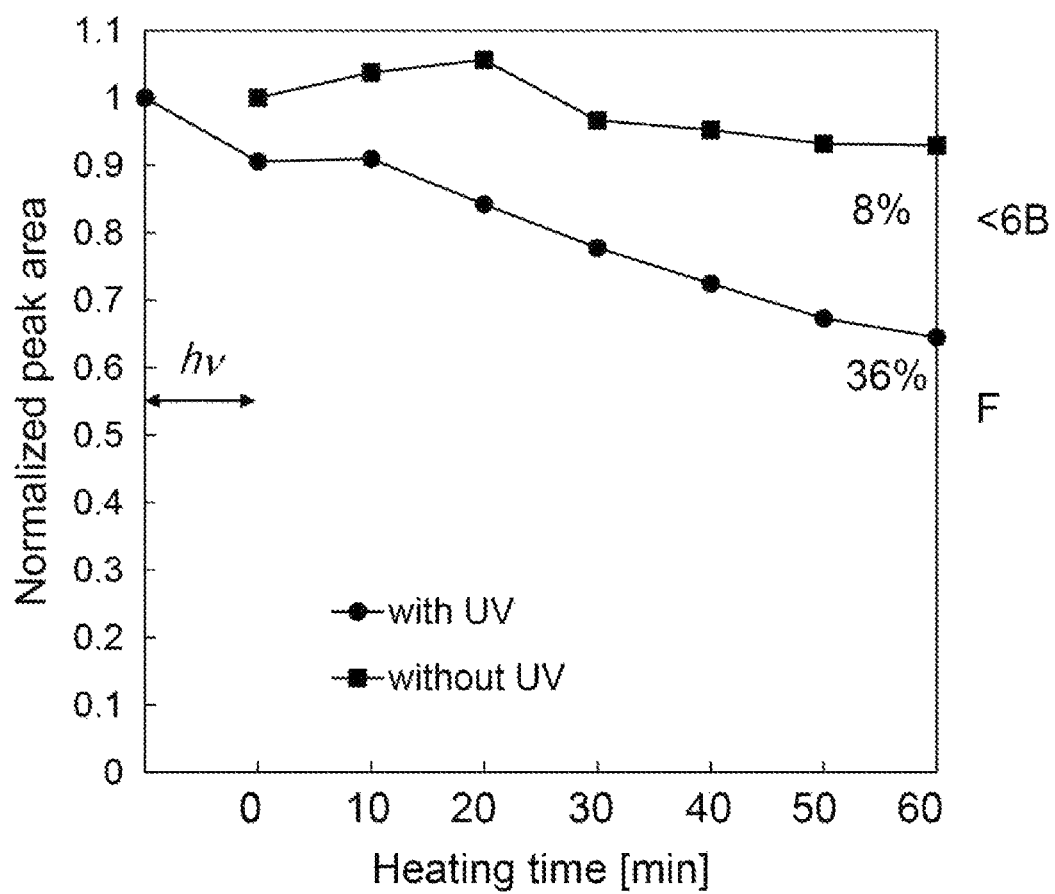
FIG. 9 is a graph that illustrates the relationship between the heating time and the peak area derived from an epoxy group under a light irradiation condition and a light non-irradiation condition in Test Example 6.

Next, a photoreactive composition using 5 mol % of the compound (1)-1 with respect to NN was used as a coating film, under the conditions (conditions for obtaining reaction product with pencil-hardness F) for obtaining a reaction product by heating at 120° C. after light irradiation, the absorption spectra were measured by a Fourier transform infrared spectrophotometer (FT-IR) under the conditions for obtaining the reaction product. The results are shown in FIG. 8. FIG. 8 shows the measurement results of the absorption spectra of the coating film before heating with the exposure doses set to 0 mJ/cm² (unirradiated) or 10000 mJ/cm², and the measurement results of the absorption spectra of the coating film heated at 120° C. for 20 minutes or 60 minutes after the exposure doses were set to 10000 mJ/cm². In FIG. 8, it was confirmed that by irradiating with light or heating, a hydroxyl group was reduced by the reaction of the compound (1)-1, an ether bond was increased by the reaction of NN, and an epoxy group was reduced by the reaction of NN After the photoreactive composition using 5 mol % of the compound (1)-1 with respect to NN was used as a coating film, and the exposure doses were set to 0 mJ/cm² (unirradiated) or the exposure doses were set to 10000 mJ/cm², the relationship between the heating time and the peak area of an epoxy group is shown in FIG. 9. As shown in FIG. 9, it was confirmed that there was a difference in the conversion rate of the epoxy group between the case of light irradiation and the case of no light irradiation.

Test Example 6

(Storage Stability of Photoreactive Composition Including Compound (1)-1 or Compound (1)-2)

The following polyfunctional aliphatic epoxy compound (EX-622) and 4-aminopyridine, 4-methylaminopyridine, the following 4-aminopyridine derivative (Urea-4APy), the compound (1)-1 or the compound (1)-2 and methanol were added into a glass test tube to prepare mixed liquids 1 to 5 as photoreactive compositions, respectively. The compositions of the mixed liquids 1 to 5 are as follows.

Mixed liquid 1 . . . EX-622 0.40 g, 4-aminopyridine 0.0046 g (5 mol % with respect to EX-622), methanol 0.40 g Mixed liquid 2 . . . EX-622 0.20 g, 4-methylaminopyridine 0.0027 g (5 mol % with respect to EX-622), methanol 0.20 g Mixed liquid 3 . . . EX-622 0.40 g, 4-aminopyridine derivative 0.011 g (5 mol % with respect to EX-622), methanol 0.41 g Mixed liquid 4 . . . EX-622 0.40 g, compound (1)-1 0.012 g (5 mol % with respect to EX-622), methanol 0.42 g Mixed liquid 5 . . . EX-622 0.10 g, compound (1)-2 0.0034 g (5 mol % with respect to EX-622), methanol 0.34 g

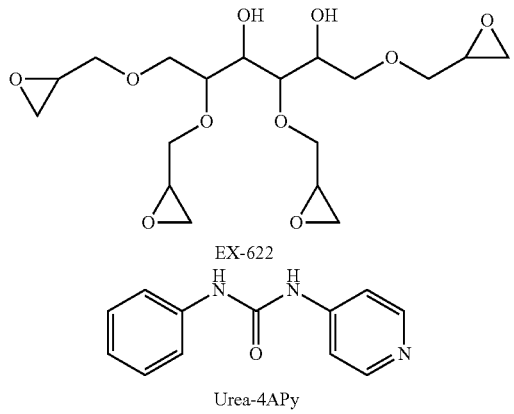

When the mixed liquids 1 to 4 were stored in a dark place at 25° C. and then shaken or inverted in a glass test tube after storage for 2 days, it was confirmed that the viscosity of the mixed liquids 1 to 4 was significantly increased. On the other hand, when the mixed liquid 5 was stored in a dark place at 25° C. and stored for 2 days and then shaken or inverted in a glass test tube, the mixed liquid 5 was a liquid with almost no increase in viscosity. When the mixed liquid 5 was stored in a dark place at 25° C. and stored for 10 days and then shaken or inverted in a glass test tube, the mixed liquid 5 was a liquid with almost no increase in viscosity.

When the mixed liquids 1 to 4 were stored in a dark place at 9° C. and then shaken or inverted in a glass test tube after storage for 24 days, the mixed liquids 1 to 4 were liquids with almost no increase in viscosity. When the mixed liquid 5 was stored in a dark place at 9° C. and then shaken or inverted in a glass test tube after storage for 10 days, the mixed liquid 5 was a liquid with almost no increase in viscosity.

Therefore, it was confirmed that the mixed liquid 4 including the compound (1)-1 was excellent in storage stability in the dark place under the cold storage condition (9° C.), and it was confirmed that the mixed liquid 5 including the compound (1)-2 was excellent in storage stability in the dark place under the room temperature condition (25° C.) and the cold storage condition (9° C.).

Test Example 7

(Evaluation of PGMA Reactivity in the Presence of 4-aminopyridine or 4-methylaminopyridine)

Polyglycidylmethyl acrylate (PGMA, 0.14 g) showing the structure below, 4-aminopyridine (0.0018 g, 2 mol % with respect to PGMA) or 4-methylaminopyridine (0.0021 g, 2 mol % with respect to PGMA) and cyclopentanone (0.71 g) were blended and stirred at 25° C. for 1 minute to obtain each photoreactive composition.

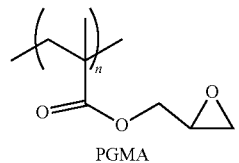

PGMA

Figure 10:
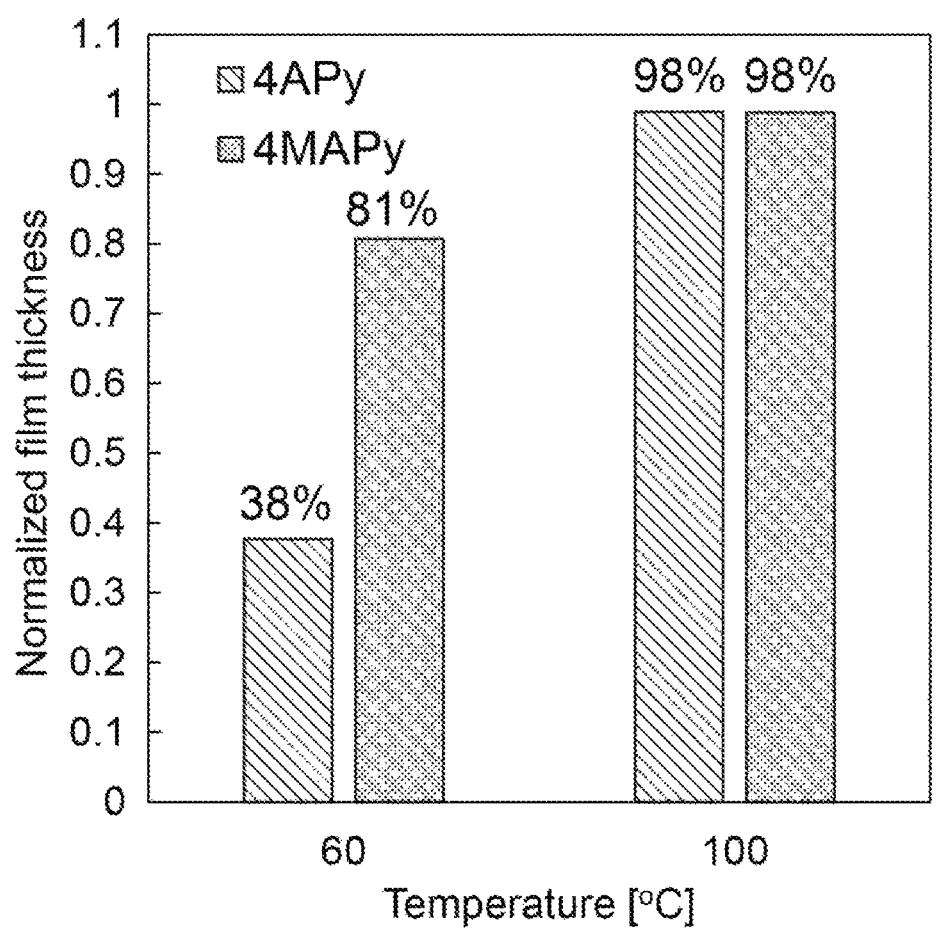
FIG. 10 is a graph that illustrates the relationship between the heating time and the normalized film thickness when using 4-aminopyridine (4APy) or 4-methyl aminopyridine (4MAPy) in Test Example 7.

Each of the photoreactive compositions obtained above was applied onto a silicon wafer by a spin coating method under the conditions of 1500 rpm and 10 seconds. Next, after heating (pre-baking) this coating film (photoreactive composition layer) at 60° C. for 1 minute, each of the coating films was heated (post-baked) 60° C. or 100° C. for 2 minutes, respectively. From the above, it was attempted to finally make each of the coating films into a reaction product obtained by polymerizing PGMA, which is an epoxy compound, and after developing with cyclohexanone for 30 seconds, the ratio (normalized film thickness) of the thickness of the reaction product after development to the coating film before heating was measured. The results are shown in FIG. 10.

Test Example 8

(Confirmation of Behavior of Compound (1)-2 in Solvent Under Light Irradiation with Wavelength of 313 nm)

Figure 11:
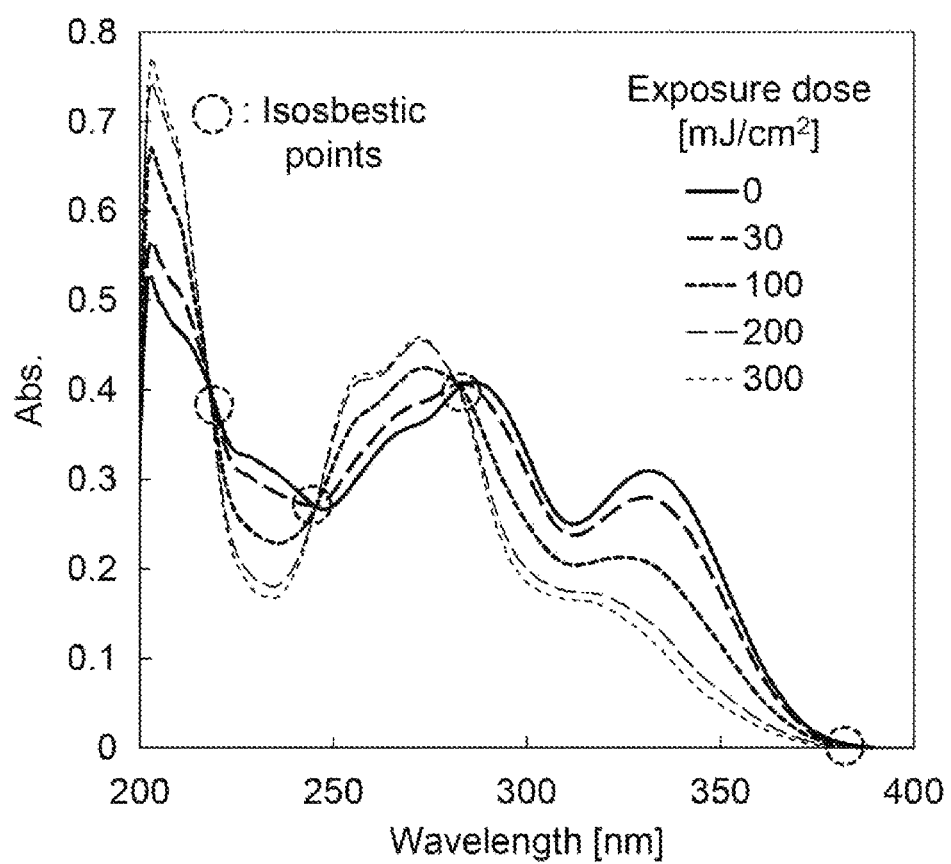
FIG. 11 is data that illustrates the measurement results of the absorbance of a compound (1)-2 in Test Example 8.

The compound (1)-2 obtained above was dissolved in methanol so as to have a concentration of $2.0\times10^{-5}$ mol/L. Then, using a mercury xenon lamp, the illuminance was set to 10 mW/cm$^2$, the exposure doses were set to 0, 30, 100, 200 and 300 mJ/cm$^2$, and the obtained methanol solution was irradiated with light having a wavelength of 313 nm. Then, the absorbance of the compound (1)-2 was measured. The result is shown in FIG. 11.

Test Example 9

(Confirmation of Behavior of Compound (1)-2 in Solvent Under Light Irradiation with a Wavelength of 365 nm)

The compound (1)-2 obtained above was dissolved in methanol so as to have a concentration of $2.0\times10^{-5}$ mol/L. Then, using an LED lamp, the illuminance was set to 10 mW/cm$^2$, the exposure doses were set to 0, 30, 100, 200 and 300 mJ/cm$^2$, and the obtained methanol solution was irradiated with light having a wavelength of 365 nm. Then, the absorbance of the compound (1)-2 was measured. The result is shown in FIG. 12.

In Test Example 8, the molar absorption coefficient was $\varepsilon_{313}=1.3\times10^4$ L/(mol·cm), and in Test Example 9, the molar absorption coefficient was $\varepsilon_{365}=3.2\times10^3$ L/(mol·cm).

Figure 12:
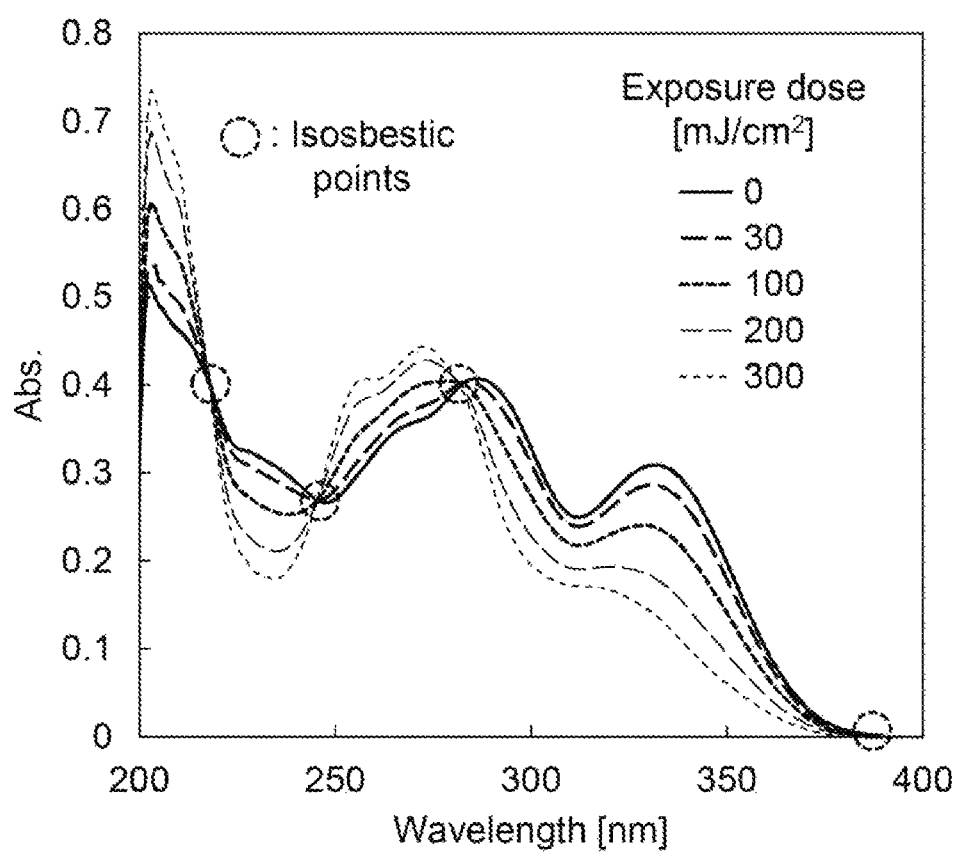
FIG. 12 is data that illustrates the measurement results of the absorbance of a compound (1)-2 in Test Example 9.

As is clear from FIG. 11 and FIG. 12, as compared with the spectrum in the case of the exposure doses of 0 mJ/cm$^2$, that is, the spectrum in the case of no light irradiation, in the spectrum for other doses, both increasing peak and decreasing peak exist, and from these measurement results, it was confirmed that a base was generated from the compound (1)-2 by light irradiation.

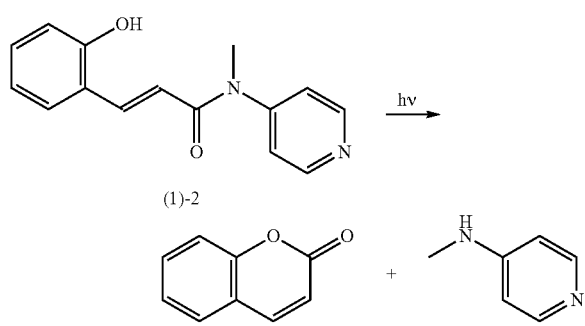

Test Example 10

(Negative Patterning Using Photoreactive Composition Including Compound (1)-2)

Polyglycidylmethyl acrylate (PGMA, 0.14 g) showing the structure above, the compound (1)-2 (0.0060 g, 2 mol % with respect to PGMA) and cyclopentanone (0.63 g) were blended and stirred at 25° C. for 1 minute to obtain a photoreactive composition.

The photoreactive composition obtained above was applied onto a silicon wafer by a spin coating method under the conditions of 1500 rpm and 10 seconds. Next, after heating (pre-baking) this coating film (photoreactive composition layer) at 60° C. for 1 minute, using an LED lamp, the coating film was irradiated with light having a wavelength of 365 nm with an illuminance of 50 mW/cm² and the exposure doses of 1000 mJ/cm² so that the light-irradiated portion and the non-irradiated portion were alternately located. After light irradiation, the coating film was heated (post-baked) 80° C. for 270 seconds. The coating film after heated was developed with cyclohexanone for 30 seconds, and then the ratio of the thickness of the coating film after development to the coating film before light irradiation was measured. As a result, the thickness of the coating film after development was 1.6 μm and the ratio (normalized film thickness) of the thickness of the coating film after development to the coating film before light irradiation was 0.96.

Test Example 11

(Production of Reaction Product Using Photoreactive Composition Including Compound (1)-2)

Polyglycidylmethyl acrylate (PGMA, 0.14 g) showing the structure above, the compound (1)-2 (0.0060 g, 2 mol % with respect to PGMA) and cyclopentanone (0.63 g) were blended and stirred at 25° C. for 1 minute to obtain a photoreactive composition.

The photoreactive compositions obtained above was applied onto a silicon wafer by a spin coating method under the conditions of 1500 rpm and 10 seconds. Next, after heating (pre-baking) this coating film (photoreactive composition layer) at 60° C. for 3 minutes, using an LED lamp, the coating film was irradiated with light having a wavelength of 365 nm with an illuminance of 50 mW/cm² and the exposure doses of 0 mJ/cm² to 1000 mJ/cm². After light irradiation, the coating film was heated (post-baked) 80° C. for 5 minutes. The coating film after heated was developed with cyclohexanone for 30 seconds, and then the ratio of the thickness of the coating film after development to the coating film before light irradiation was measured. The results are shown in FIG. 13.

Figure 13:
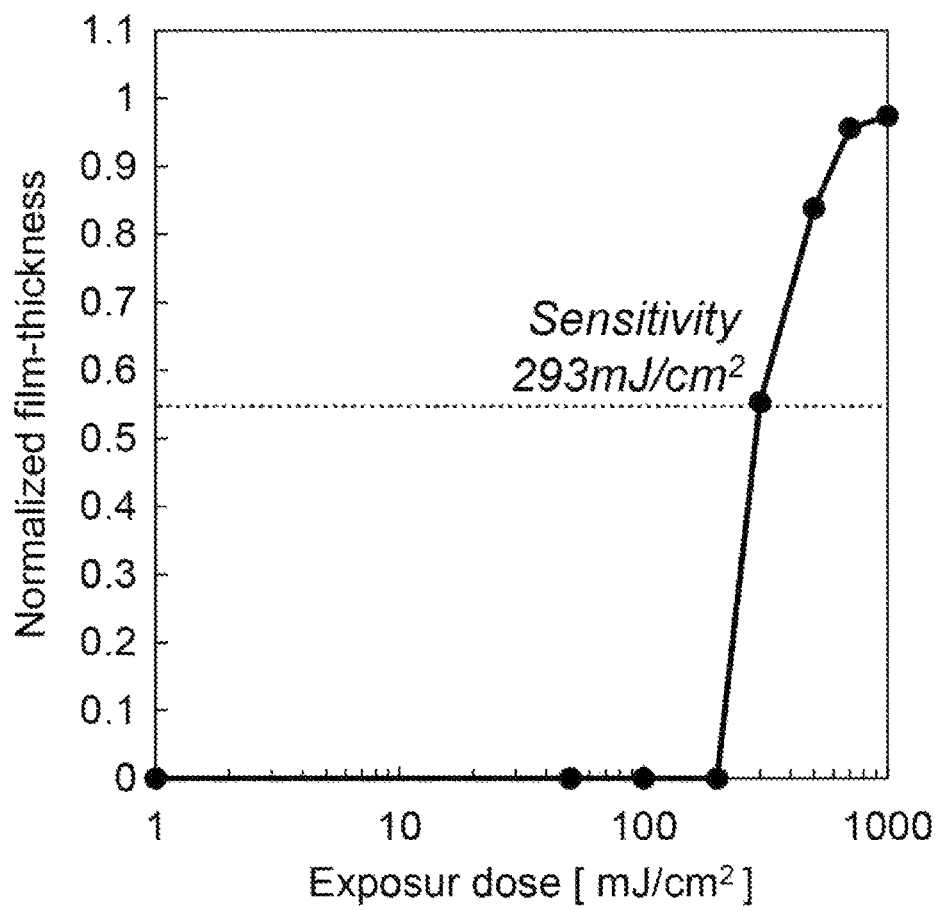
FIG. 13 is a graph that illustrates the relationship between the exposure doses and the normalized film thickness in Test Example 11.

As shown in FIG. 13, the exposure doses at the gel point (for example, the point where the residual film is generated) was 200 mJ/cm², and the exposed doses at which the normalized film thickness was about 0.55 were 293 mJ/cm². When the exposure doses were 1000 mJ/cm², the normalized film thickness was 0.98.

<Production of Compound (2)>

At first, as shown below, trans-o-coumaric acid was reacted with cyclohexylamine to produce a compound (2). In practice, trans-o-coumaric acid (4.00 g) and cyclohexylamine (3.63 g) were added to a mixture liquid obtained by mixing 60 mL of N, N-dimethylformamide (DMF) and 9.35 g of N-ethyl-N'-dimethylaminopropylcarbodiimide (EDAC), and was stirred at room temperature for 24 hours to produce the compound (2).

The compound (2) produced was washed to obtain the objective compound (2) as a white solid (yield 24%).

Regarding the obtained compound (2), the analysis results of $^1$H-NMR, and $^{13}$C-NMR are shown in Table 3.

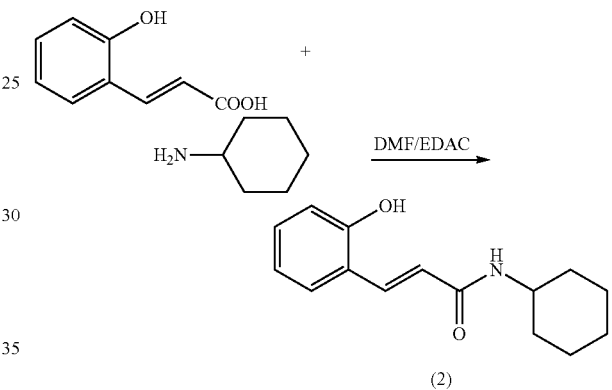

TABLE 3

| $^1$H-NMR [δ/ppm] [300 MHz, DMSO] | 10.0 (s, 1H, OH), 7.93 (d, J = 7.6 Hz, 1H, —NH—), 7.60 (d, J = 15 Hz, 1H, CH=C̲HCO), 7.41-6.80 (m, 4H, Ar—H), 6.64 (d, J = 15 Hz, 1H, C̲H=CHCO), 3.35 (d, J = 7.6 Hz, 1H, —N—CH—), 1.80-0.84 (m, 10H, —CH$_2$—) |
|---|---|
| $^{13}$C-NMR [δ/ppm] [75 MHz, DMSO] | 164.5 (C=O), 156.3 (CH), 134.2, 130.2, 131.8, 128.0, 122.0, 121.8 (Ar—H), 116.1 (CH), 47.5, 32.5, 25.2, 24.6 (CH$_2$) |

Test Example 12

(Production of Reaction Product Using Photoreactive Composition Including Compound (2))

Polyglycidylmethyl acrylate (PGMA, 0.1 g, molecular weight; 22000) showing the structure above, the compound (2) (0.005 g) and tetrahydrofuran (1 g) were blended and stirred at 25° C. for 1 minute to obtain a photoreactive composition.

The photoreactive compositions obtained above was applied onto a silicon wafer by a spin coating method under the conditions of 1500 rpm and 30 seconds. Next, after heating (pre-baking) this coating film (photoreactive composition layer) at 100° C. for 1 minutes, using a Hg—Xe lamp, the coating film was irradiated with light having a wavelength of 365 nm with an illuminance of 50 mW/cm² and the exposure doses of 0 mJ/cm² to 10000 mJ/cm². After light irradiation, the coating film was heated (post-baked) 160° C. for 20 minutes. The coating film after heated was developed with tetrahydrofuran for 30 seconds, and then the ratio of the thickness of the coating film after development to the coating film before light irradiation was measured. It was attempted to measure the normalized film thickness of each coating film after development with the exposure doses of 100 mJ/cm$^2$, 1000 mJ/cm$^2$ and 10000 mJ/cm$^2$, but the normalized film thickness was 0% in each film, and an insolubilized reaction product could not be produced from the photoreactive composition including the compound (2).

The disclosure of Japanese Patent Application No. 2019-237416 filed on Dec. 26, 2019 is herein incorporated by reference in its entity.

All documents, patent applications, and technical standards described herein are herein incorporated by reference, as if each individual document, patent application, and technical standard were specifically and individually indicated to be incorporated by reference.

The invention claimed is:

1. A compound comprising:
a first skeleton represented by the following formula (a); and
a second skeleton including a nitrogen atom bonding to a bonding position of the first skeleton to form an amide group, and a pyridine skeleton in addition to the nitrogen atom, and the second skeleton represented by the following formula (C),
wherein the compound generates a base in which a hydrogen atom is bonded with the nitrogen atom of the second skeleton by light irradiation:

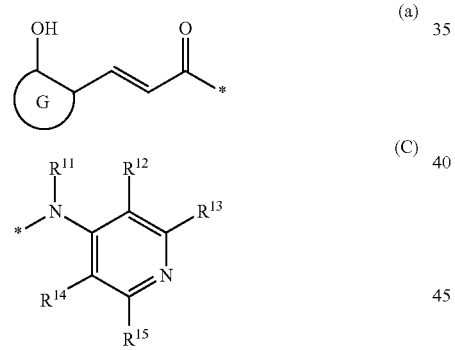

wherein, in formula (a), G is a divalent aromatic group, and * represents the bonding position with the nitrogen atom, and in the formula (C), $R^{11}$ represents a hydrogen atom, or an alkyl group, each of $R^{12}$ to $R^{15}$ independently represents a hydrogen atom, an alkyl group, an alkoxy group, an aryloxy group, a dialkylamino group, a diarylamino group, an alkylarylamino group, an alkylcarbonyl group, an arylcarbonyl group, an alkyloxycarbonyl group, an aryloxycarbonyl group, an alkylcarbonyloxy group, an arylcarbonyloxy group, an alkylthio group, an arylthio group, a cyano group (—CN), a halogen atom, a nitro group, a haloalkyl group (halogenated alkyl group), a hydroxyl group (—OH), a mercapto group (—SH), an amino group, an aromatic hydrocarbon group, or an aromatic heterocyclic group, and * represents the bonding position with * of the formula (a), and
wherein the second skeleton includes an aminopyridine skeleton.

2. A photobase generator comprising the compound according to claim 1.

3. A photoreactive composition, comprising:
a photobase generator; and
a base-reactive compound,
wherein the base-reactive compound is a compound having a functional group that is converted, by action of a base, into a group exhibiting reactivity, or a compound having a group that reacts in response to action of a base, and
wherein the photobase generator comprises a compound including:
a first skeleton represented by the following formula (a); and
a second skeleton including a nitrogen atom bonding to a bonding position of the first skeleton to form an amide group, and a pyridine skeleton in addition to the nitrogen atom,
wherein the compound generates a base in which a hydrogen atom is bonded with the nitrogen atom of the second skeleton by light irradiation:

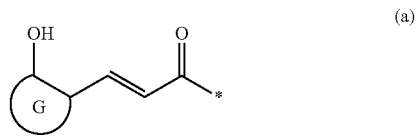

wherein, in formula (a), G is a divalent aromatic group, and * represents the bonding position with the nitrogen atom.

4. A reaction product obtained by reacting the photoreactive composition according to claim 3.

5. A photoreactive composition, comprising:
a photobase generator; and
a base-reactive compound,
wherein the base-reactive compound is a compound having a functional group that is converted, by action of a base, into a group exhibiting reactivity, or a compound having a group that reacts in response to action of a base, and
wherein the photobase generator comprises a compound including:
a first skeleton represented by the following formula (a); and
a second skeleton including a nitrogen atom bonding to a bonding position of the first skeleton to form an amide group, and a pyridine skeleton in addition to the nitrogen atom,
wherein the compound generates a base in which a hydrogen atom is bonded with the nitrogen atom of the second skeleton by light irradiation:

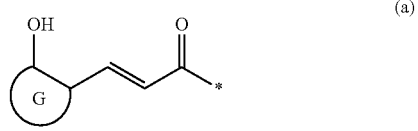

wherein, in formula (a), G is a divalent aromatic group, and * represents the bonding position with the nitrogen atom, and wherein the second skeleton includes an aminopyridine skeleton.

* * * * *